US010426317B2

(12) United States Patent
Michihata et al.

(10) Patent No.: US 10,426,317 B2
(45) Date of Patent: Oct. 1, 2019

(54) MEDICAL SIGNAL PROCESSING DEVICE AND MEDICAL OBSERVATION SYSTEM

(71) Applicant: SONY OLYMPUS MEDICAL SOLUTIONS INC., Tokyo (JP)

(72) Inventors: Taihei Michihata, Kanagawa (JP); Yuichi Yamada, Tokyo (JP)

(73) Assignee: Sony Olympus Medical Solutions Inc., Tokyo (JP)

( * ) Notice: Subject to any disclaimer, the term of this patent is extended or adjusted under 35 U.S.C. 154(b) by 210 days.

(21) Appl. No.: 15/384,810

(22) Filed: Dec. 20, 2016

(65) Prior Publication Data

US 2017/0202432 A1 Jul. 20, 2017

(30) Foreign Application Priority Data

Jan. 15, 2016 (JP) ................................ 2016-006645

(51) Int. Cl.

*H04N 5/225* (2006.01)
*A61B 1/00* (2006.01)
*A61B 1/04* (2006.01)

(52) U.S. Cl.

CPC ...... *A61B 1/00009* (2013.01); *A61B 1/00006* (2013.01); *A61B 1/00013* (2013.01); *A61B 1/00045* (2013.01); *A61B 1/00055* (2013.01); *A61B 1/04* (2013.01); *H04N 5/2256* (2013.01); *H04N 2005/2255* (2013.01)

(58) Field of Classification Search

None

See application file for complete search history.

(56) References Cited

U.S. PATENT DOCUMENTS

2009/0210754 A1* 8/2009 Sekiguchi ............. G06F 11/327 714/57
2011/0183698 A1* 7/2011 Hoctor .............. H04W 72/1252 455/509
2013/0258147 A1* 10/2013 Kachi ...................... H04N 9/07 348/280
2014/0309491 A1* 10/2014 Karasawa .......... A61B 1/00124 600/103

FOREIGN PATENT DOCUMENTS

JP 2006-26134 2/2006
JP 2009-61032 3/2009

* cited by examiner

*Primary Examiner* — Mohammed S Rahaman
(74) *Attorney, Agent, or Firm* — Oblon, McClelland, Maier & Neustadt, L.L.P.

(57) ABSTRACT

A medical signal processing device receives an image signal in accordance with a result of examining inside of a subject and processes the image signal. The medical signal processing device includes a signal processing unit configured to generate a plurality of transmission image signals from the image signal. The transmission image signals each include a plurality of distributed image signals obtained by distributing the image signal, at least any of the transmission image signals includes, as auxiliary data, data of at least part of distributed image signals different from the distributed image signals included in the transmission image signal, and the transmission image signals are transmitted to an external medical control device through a plurality of respective signal transmission paths.

12 Claims, 30 Drawing Sheets

| 0<br>(CA) | 1<br>(CB) | 2<br>(CC) | 3<br>(CD) | 4<br>(CE) | 5<br>(CF) | 6<br>(CG) | 7<br>(CH) | 8<br>(CI) | 9<br>(CJ) | 10<br>(CA) | ...... |
|---|---|---|---|---|---|---|---|---|---|---|---|
| △△<br>(CA) | △□<br>(CB) | △○<br>(CC) | △×<br>(CD) | □□<br>(CE) | □△<br>(CF) | □○<br>(CG) | □×<br>(CH) | ○△<br>(CI) | ○□<br>(CJ) | ○×<br>(CA) | ...... |

| | | | | | | | | | | |
|---|---|---|---|---|---|---|---|---|---|---|
| (a) FIRST CHANNEL CA | 0 (9) | 0 (8) | 0 (7) | 0 (6) | 0 (5) | 0 (4) | 0 (3) | 0 (2) | 0 (1) | 0 (0) |
| (b) SECOND CHANNEL CB | 1 (9) | 1 (8) | 1 (7) | 1 (6) | 1 (5) | 1 (4) | 1 (3) | 1 (2) | 1 (1) | 1 (0) |
| (c) THIRD CHANNEL CC | 2 (9) | 2 (8) | 2 (7) | 2 (6) | 2 (5) | 2 (4) | 2 (3) | 2 (2) | 2 (1) | 2 (0) |
| (d) FOURTH CHANNEL CD | 3 (9) | 3 (8) | 3 (7) | 3 (6) | 3 (5) | 3 (4) | 3 (3) | 3 (2) | 3 (1) | 3 (0) |
| (e) FIFTH CHANNEL CE | 4 (9) | 4 (8) | 4 (7) | 4 (6) | 4 (5) | 4 (4) | 4 (3) | 4 (2) | 4 (1) | 4 (0) |
| (f) SIXTH CHANNEL CF | 5 (9) | 5 (8) | 5 (7) | 5 (6) | 5 (5) | 5 (4) | 5 (3) | 5 (2) | 5 (1) | 5 (0) |
| (g) SEVENTH CHANNEL CG | 6 (9) | 6 (8) | 6 (7) | 6 (6) | 6 (5) | 6 (4) | 6 (3) | 6 (2) | 6 (1) | 6 (0) |
| (h) EIGHTH CHANNEL CH | 7 (9) | 7 (8) | 7 (7) | 7 (6) | 7 (5) | 7 (4) | 7 (3) | 7 (2) | 7 (1) | 7 (0) |
| (i) NINTH CHANNEL CI | 8 (9) | 8 (8) | 8 (7) | 8 (6) | 8 (5) | 8 (4) | 8 (3) | 8 (2) | 8 (1) | 8 (0) |
| (j) TENTH CHANNEL CJ | 9 (9) | 9 (8) | 9 (7) | 9 (6) | 9 (5) | 9 (4) | 9 (3) | 9 (2) | 9 (1) | 9 (0) |

| | FS1 | FS2 | FS3 | FS4 | FS5 | FS6 | FS7 | FS8 | FS9 | FS10 |
|---|---|---|---|---|---|---|---|---|---|---|
| | SAV1 | SAV1 | SAV1 | SAV1 | SAV1 | SAV1 | SAV1 | SAV1 | SAV1 | SAV1 |
| | SAV2 | SAV2 | SAV2 | SAV2 | SAV2 | SAV2 | SAV2 | SAV2 | SAV2 | SAV2 |
| | SAV3 | SAV3 | SAV3 | SAV3 | SAV3 | SAV3 | SAV3 | SAV3 | SAV3 | SAV3 |
| | SAV4 | SAV4 | SAV4 | SAV4 | SAV4 | SAV4 | SAV4 | SAV4 | SAV4 | SAV4 |
| | 0 | 1 | 2 | 3 | 4 | 5 | 6 | 7 | 8 | 9 |
| | 10 | 11 | 12 | 13 | 14 | 15 | 16 | 17 | 18 | 19 |
| | 20 | 21 | 22 | 23 | 24 | 25 | 26 | 27 | 28 | 29 |
| | 30 | 31 | 32 | 33 | 34 | 35 | 36 | 37 | 38 | 39 |
| | 40 | 41 | 42 | 43 | 44 | 45 | 46 | 47 | 48 | 49 |
| | 50 | 51 | 52 | 53 | 54 | 55 | 56 | 57 | 58 | 59 |
| | 60 | 61 | 62 | 63 | 64 | 65 | 66 | 67 | 68 | 69 |
| | 70 | 71 | 72 | 73 | 74 | 75 | 76 | 77 | 78 | 79 |
| | 80 | 81 | 82 | 83 | 84 | 85 | 86 | 87 | 88 | 89 |
| | 90 | 91 | 92 | 93 | 94 | 95 | 96 | 97 | 98 | 99 |
| | 100 | 101 | 102 | 103 | 104 | 105 | 106 | 107 | 108 | 109 |
| | 110 | 111 | 112 | 113 | 114 | 115 | 116 | 117 | 118 | 119 |
| | 120 | 121 | 122 | 123 | 124 | 125 | 126 | 127 | 128 | 129 |
| | 130 | 131 | 132 | 133 | 134 | 135 | 136 | 137 | 138 | 139 |
| | 140 | 141 | 142 | 143 | 144 | 145 | 146 | 147 | 148 | 149 |
| | 150 | 151 | 152 | 153 | 154 | 155 | 156 | 157 | 158 | 159 |
| | 160 | 161 | 162 | 163 | 164 | 165 | 166 | 167 | 168 | 169 |
| | ⋮ | ⋮ | ⋮ | ⋮ | ⋮ | ⋮ | ⋮ | ⋮ | ⋮ | ⋮ |
| | 4190 | 4191 | 4192 | 4193 | 4194 | 4195 | 4196 | 4197 | 4198 | 4199 |
| | 4200 | 4201 | 4202 | 4203 | 4204 | 4205 | 4206 | 4207 | 4208 | 4209 |
| | 4210 | 4211 | 4212 | 4213 | 4214 | 4215 | 4216 | 4217 | 4218 | 4219 |
| | 4220 | 4221 | 4222 | 4223 | 4224 | 4225 | 4226 | 4227 | 4228 | 4229 |
| | 4230 | 4231 | 4232 | 4233 | 4234 | 4235 | 4236 | 4237 | 4238 | 4239 |
| | 4240 | 4241 | 4242 | 4243 | 4244 | 4245 | 4246 | 4247 | 4248 | 4249 |
| | EAV1 | EAV1 | EAV1 | EAV1 | EAV1 | EAV1 | EAV1 | EAV1 | EAV1 | EAV1 |
| | EAV2 | EAV2 | EAV2 | EAV2 | EAV2 | EAV2 | EAV2 | EAV2 | EAV2 | EAV2 |
| | EAV3 | EAV3 | EAV3 | EAV3 | EAV3 | EAV3 | EAV3 | EAV3 | EAV3 | EAV3 |
| | EAV4 | EAV4 | EAV4 | EAV4 | EAV4 | EAV4 | EAV4 | EAV4 | EAV4 | EAV4 |
| | (a) | (b) | (c) | (d) | (e) | (f) | (g) | (h) | (i) | (j) |

MEDICAL SIGNAL PROCESSING DEVICE AND MEDICAL OBSERVATION SYSTEM

CROSS-REFERENCE TO RELATED APPLICATION(S)

The present application claims priority to and incorporates by reference the entire contents of Japanese Patent Application No. 2016-006645 filed in Japan on Jan. 15, 2016.

BACKGROUND

The present disclosure relates to a medical signal processing device, and a medical observation system including the medical signal processing device.

Medical observation systems in the medical field are configured to capture an image of the inside of a subject such as a human (inside of a living body) to observe the inside of this living body (for example, refer to Japanese Patent Laid-open No. 2009-61032 and Japanese Patent Laid-open No. 2006-26134).

Medical observation systems disclosed in Japanese Patent Laid-open No. 2009-61032 and Japanese Patent Laid-open No. 2006-26134 ("electronic endoscope systems" in Japanese Patent Laid-open No. 2009-61032 and Japanese Patent Laid-open No. 2006-26134) each include a medical observation device ("electronic endoscope" in Japanese Patent Laid-open No. 2009-61032 and Japanese Patent Laid-open No. 2006-26134) configured to capture an image of the inside of a living body and output an image signal, a control device ("video processor" in Japanese Patent Laid-open No. 2009-61032 and "processor" in Japanese Patent Laid-open No. 2006-26134) configured to receive the image signal from the medical observation device and process the image signal to generate a display image signal, and a signal transmission path ("wireless connector" in Japanese Patent Laid-open No. 2009-61032 and "signal line" in Japanese Patent Laid-open No. 2006-26134) through which the image signal from the medical observation device is transmitted to the control device.

SUMMARY

When a failure occurs in transmission of the image signal due to, for example, breaking of the signal transmission path, the control device is unable to appropriately generate the display image signal and display an image suitable for observation.

In the medical observation system disclosed in Japanese Patent Laid-open No. 2009-61032, when a signal transmission state in the signal transmission path is detected and the detected transmission state is inappropriate for transmission, an operator is warned or notified by, for example, a buzzer. However, in the medical observation system disclosed in Japanese Patent Laid-open No. 2009-61032, an image suitable for observation may not be displayed until the signal transmission path is replaced by, for example, the operator in response to this warning or notification.

The medical observation system disclosed in Japanese Patent Laid-open No. 2006-26134 is provided with at least two signal transmission paths through which an identical image signal is transmitted. With this configuration, in the medical observation system disclosed in Japanese Patent Laid-open No. 2006-26134, when a transmission failure occurs in one of the signal transmission paths, the image signal may be transmitted to the control device through the other signal transmission path, which achieves continuous display of an image suitable for observation. However, one of the signal transmission paths is unnecessary when no transmission failure occurs. In other words, in the medical observation system disclosed in Japanese Patent Laid-open No. 2006-26134, the above-described signal transmission path needs to be redundantly provided, which prevents simplification of the structure.

There is a need for a technique of performing, with a simplified structure, continuous display of an image suitable for observation when a transmission failure occurs in a signal transmission path.

According to one aspect of the present disclosure, there is provided a medical signal processing device for receiving an image signal in accordance with a result of examining inside of a subject and processing the image signal, the medical signal processing device including: a signal processing unit configured to generate a plurality of transmission image signals from the image signal, wherein the transmission image signals each include a plurality of distributed image signals obtained by distributing the image signal, at least any of the transmission image signals includes, as auxiliary data, data of at least part of distributed image signals different from the distributed image signals included in the transmission image signal, and the transmission image signals are transmitted to an external medical control device through a plurality of respective signal transmission paths.

BRIEF DESCRIPTION OF THE DRAWINGS

FIG. 3B is a diagram illustrating the image signal output from the imaging unit illustrated in FIG. 2;

DETAILED DESCRIPTION

Figure 1:
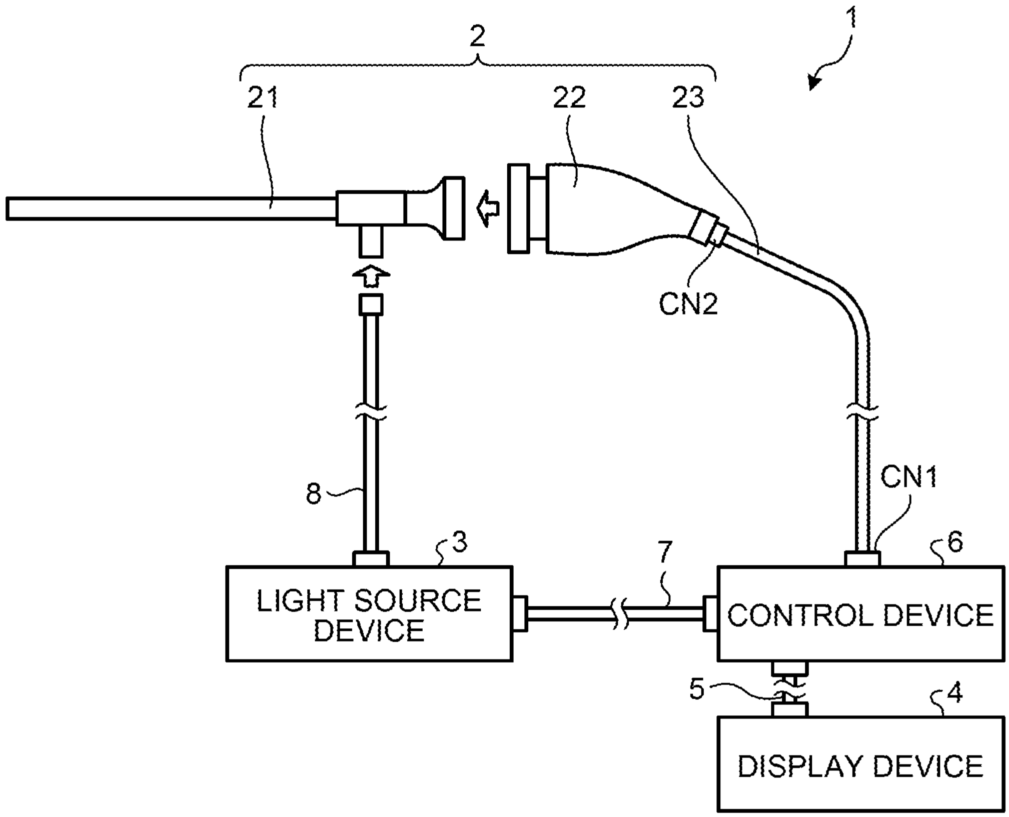
FIG. 1 is a diagram illustrating a schematic configuration of a medical observation system according to a first embodiment of the present disclosure.

Configurations to achieve the present disclosure (hereinafter referred to as embodiments) will be described below with reference to the accompanying drawings. The embodiments described below, however, are not intended to limit the present disclosure. In description of the drawings, any identical parts are denoted by an identical reference numeral.

First Embodiment

Schematic Configuration of Medical Observation System

FIG. 1 is a diagram illustrating a schematic configuration of a medical observation system 1 according to a first embodiment of the present disclosure.

The medical observation system 1 is used in the medical field to observe the inside of a subject such as a human (inside of a living body). As illustrated in FIG. 1, the medical observation system 1 includes an endoscope 2, a light source device 3, a display device 4, a second transmission cable 5, a control device 6, a third transmission cable 7, and a light guide 8.

The endoscope 2 examines the inside of the living body and outputs an image signal (a plurality of transmission image signals) in accordance with a result of this examination. As illustrated in FIG. 1, the endoscope 2 includes an insertion unit 21, a camera head 22, and a first transmission cable 23.

The insertion unit 21 is hard or at least partially soft, has an elongated shape, and is inserted into the inside of the living body. The insertion unit 21 includes an optical system that includes one or a plurality of lenses and through which an object image is condensed.

The light source device 3 is connected with one end of the light guide 8, and supplies, under control of the control device 6, this one end of the light guide 8 with light for illumination of the inside of the living body.

The light guide 8 has one end detachably connected with the light source device 3 and the other end detachably connected with the insertion unit 21. The light guide 8 transfers the light supplied by the light source device 3 from the one end to the other end to supply the light to the insertion unit 21. The light supplied to the insertion unit 21 is emitted from a leading end of the insertion unit 21 and incident on the inside of the living body. The light (object image) incident on the inside of the living body is condensed through the optical system in the insertion unit 21.

The camera head 22 is detachably connected with a base end of the insertion unit 21. The camera head 22 captures, under control of the control device 6, the object image condensed through the insertion unit 21 and generates an image capturing signal (image signal). The camera head 22 also generates a plurality of transmission image signals from this image signal and outputs these transmission image signals. In the first embodiment, the camera head 22 converts these transmission image signals into optical signals and outputs these transmission image signals as the optical signals.

The configuration of the camera head 22 will described later in detail.

The first transmission cable 23 has one end detachably connected with the control device 6 through a connector CN1 (FIG. 1) and the other end connected with the camera head 22 through a connector CN2 (FIG. 1). Specifically, the first transmission cable 23 includes a plurality of electric wires 231 (refer to FIG. 2) and a plurality of optical fibers 232 (refer to FIG. 2) arranged inside of an outer cover, which is an outermost layer.

Figure 2:
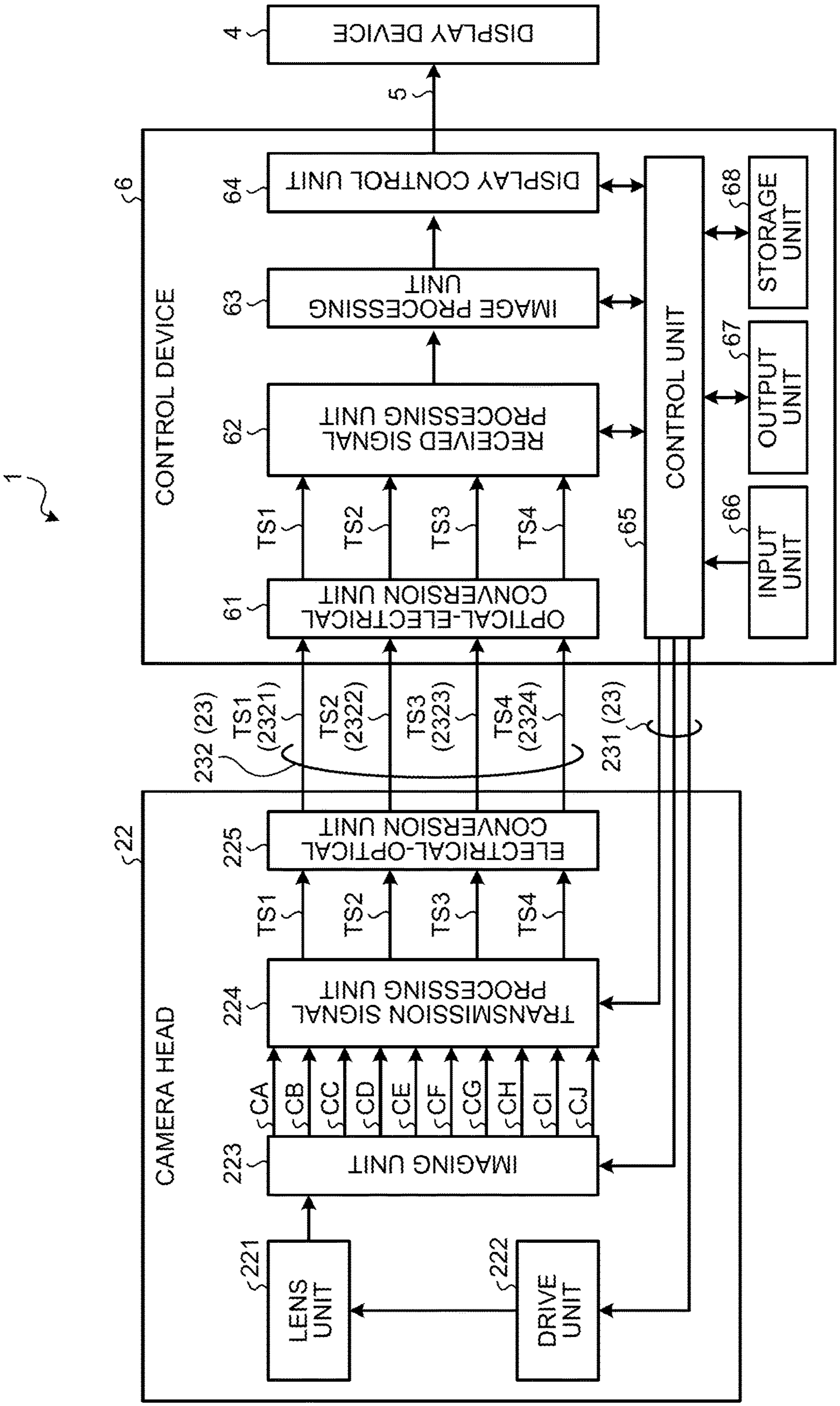
FIG. 2 is a block diagram of the configurations of a camera head and a control device illustrated in FIG. 1.

The electric wires 231 are electric wires for transmitting, for example, a control signal, a synchronizing signal, a clock, and electrical power output from the control device 6 to the camera head 22. In FIG. 2, the number of the electric wires 231 is three but not limited thereto, and may be any other number.

The optical fibers 232 are optical fibers for transmitting, to the control device 6, the transmission image signals (optical signals) output from the camera head 22. In the first embodiment, the four optical fibers 232 of first to fourth optical fibers 2321 to 2324 (refer to FIG. 2) are provided. The number of the provided optical fibers 232 depends on the number of optical signals output from the camera head 22 and is changed in accordance with any change in the number of optical signals.

The optical fibers 232 included in the first transmission cable 23 each function as a signal transmission path according to the present disclosure.

The display device 4 includes a display exploiting, for example, liquid crystal or organic electro luminescence (EL), and displays an image based on image signals processed at the control device 6.

The second transmission cable 5 has one end detachably connected with the display device 4 and the other end detachably connected with the control device 6. The second transmission cable 5 transmits image signals processed at the control device 6 to the display device 4.

The control device 6 includes, for example, a central processing unit (CPU) and performs overall control of operation of the light source device 3, the camera head 22, and the display device 4.

The configuration of the control device 6 will be described later in detail.

The third transmission cable 7 has one end detachably connected with the light source device 3 and the other end detachably connected with the control device 6. The third transmission cable 7 transmits, to the light source device 3, a control signal from the control device 6.

Configuration of Camera Head

The following describes the configuration of the camera head 22.

FIG. 2 is a block diagram of the configurations of the camera head 22 and the control device 6.

For the purpose of description, FIG. 2 omits illustrations of the connectors CN1 and CN2 connecting the control device 6 and the camera head 22 with the first transmission cable 23, and connectors connecting the control device 6 and the display device 4 with the second transmission cable 5.

As illustrated in FIG. 2, the camera head 22 includes a lens unit 221, a drive unit 222, an imaging unit 223, a transmission signal processing unit 224, and an electrical-optical conversion unit 225.

The lens unit 221 includes one or a plurality of lenses movable along an optical axis and images the object image condensed through the insertion unit 21 onto an imaging plane of the imaging unit 223 (an image sensor 2231 (refer to FIG. 3A)). The lens unit 221 is provided with an optical zoom mechanism (not illustrated) that changes an angle of view by moving the one or plurality of lenses, and a focus mechanism (not illustrated) that changes focus.

The drive unit 222 operates, under control of the control device 6, the optical zoom mechanism and the focus mechanism described above to change the angle of view and the focus of the lens unit 221.

The imaging unit 223 images the inside of the living body under control of the control device 6. The imaging unit 223 includes a sensor chip on which, for example, the image sensor 2231 (refer to FIG. 3A), such as a charge-coupled device (CCD) or a complementary metal oxide semiconductor (CMOS), configured to receive the object image condensed through the insertion unit 21 and imaged through the lens unit 221 and convert the object image into an electric signal, and a signal processing unit (not illustrated) configured to perform signal processing (such as A/D conversion) on the electric signal (analog signal) from the image sensor 2231 to output an image signal are integrally formed, and outputs the image signal (digital signal) after the A/D conversion. The signal processing unit (not illustrated) described above does not need to be formed integrally with the image sensor 2231 but may be formed separately.

In the first embodiment, the imaging unit 223 outputs the image signal after the A/D conversion through 10 channels (first to tenth channels CA to CJ (FIG. 2)) in parallel. The number of channels is not limited to 10 but may be any other number.

The image signal from the imaging unit 223 according to the first embodiment may be output as differential signals for the respective channels. In this case, for example, the signal processing unit (not illustrated) described above may be provided with a differential conversion unit (not illustrated) configured to convert the image signal after the A/D conversion into differential signals, and the transmission signal processing unit 224 to be described later may be provided with a restoring unit (not illustrated) configured to restore the differential signals to the original image signal.

Figure 3A:
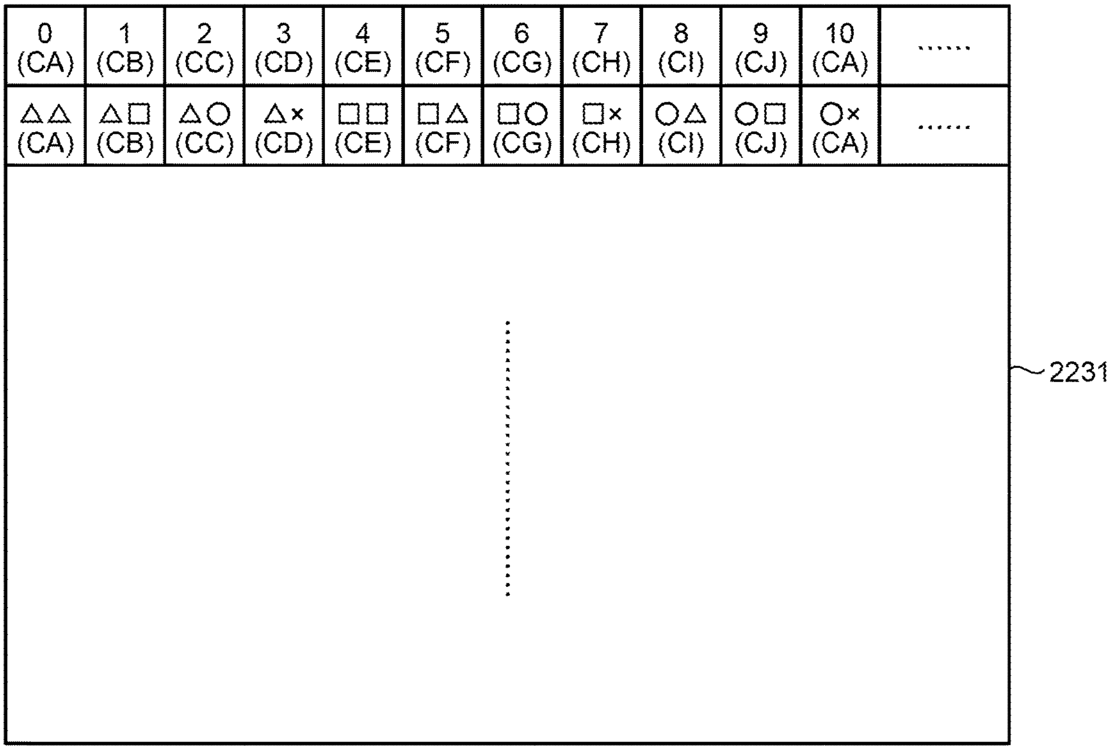
FIG. 3A is a diagram illustrating an image signal output from an imaging unit illustrated in FIG. 2.

FIGS. 3A and 3B are each a diagram illustrating the image signal output from the imaging unit 223. Specifically, FIG. 3A is a diagram illustrating a physical arrangement of effective pixels of the image sensor 2231. FIG. 3B is a diagram illustrating the image signal output from the imaging unit 223.

The number of bits per pixel in the image signal output from the imaging unit 223 is 10 in the first embodiment, but may be any other number.

In FIG. 3A, pixels on the first row are denoted by sequential numbers (address numbers of "0", "1", "2", . . . ) starting at the first column. Pixels at the second row are denoted by sequential address numbers (illustrated as, for example, a triangle in FIG. 3A) starting at the first column and following the address number of the pixel at the last column on the first row. The same notation applies to the third row and the following rows. In FIG. 3A, each pixel is denoted by such an address number followed by a reference sign ("CA" to "CJ") in parentheses, of any of the first to the tenth channels CA to CJ through which pixel data generated at this pixel is output. In addition, (a) to (j) in FIG. 3B illustrate pixel data (in FIG. 3B, for sake of simplicity, pixel data of pixels at address numbers "0" to "9") output through the first to the tenth channels CA to CJ. In FIG. 3B, an address number indicating a pixel at which pixel data is obtained is provided at each bit position of this pixel data, followed by this bit position (with a most significant bit (MSB; the bit position of a most significant digit) of "9" and a least significant bit (LSB; the bit position of a least significant digit) of "0" in parentheses.

In the first embodiment, as illustrated in FIGS. 3A and 3B, the imaging unit 223 converts pixel data generated at the pixel of address number "0" into serial data, and outputs the serial data bit by bit sequentially from the MSB through the first channel CA. The imaging unit 223 also converts pixel data generated at the pixel of address number "1" into serial data, and outputs the serial data bit by bit sequentially from the MSB through the second channel CB. Similarly, the imaging unit 223 converts each piece of pixel data generated at the pixels of address numbers "2" to "9" into serial data, and outputs the serial data bit by bit sequentially from the MSB through the third to the tenth channels CC to CJ.

In the pieces of pixel data vertically arranged in FIG. 3B, pieces of data at an identical bit position are output simultaneously through the first to the tenth channels CA to CJ, respectively.

Specifically, the imaging unit 223 outputs, in parallel through the first to the tenth channels CA to CJ as described above, pieces of pixel data (serial data) generated at 10 pixels each in an order of the address number.

In the first embodiment, as illustrated in FIG. 3A, pieces of pixel data generated at pixels at an identical column are output through an identical channel.

Figure 5:
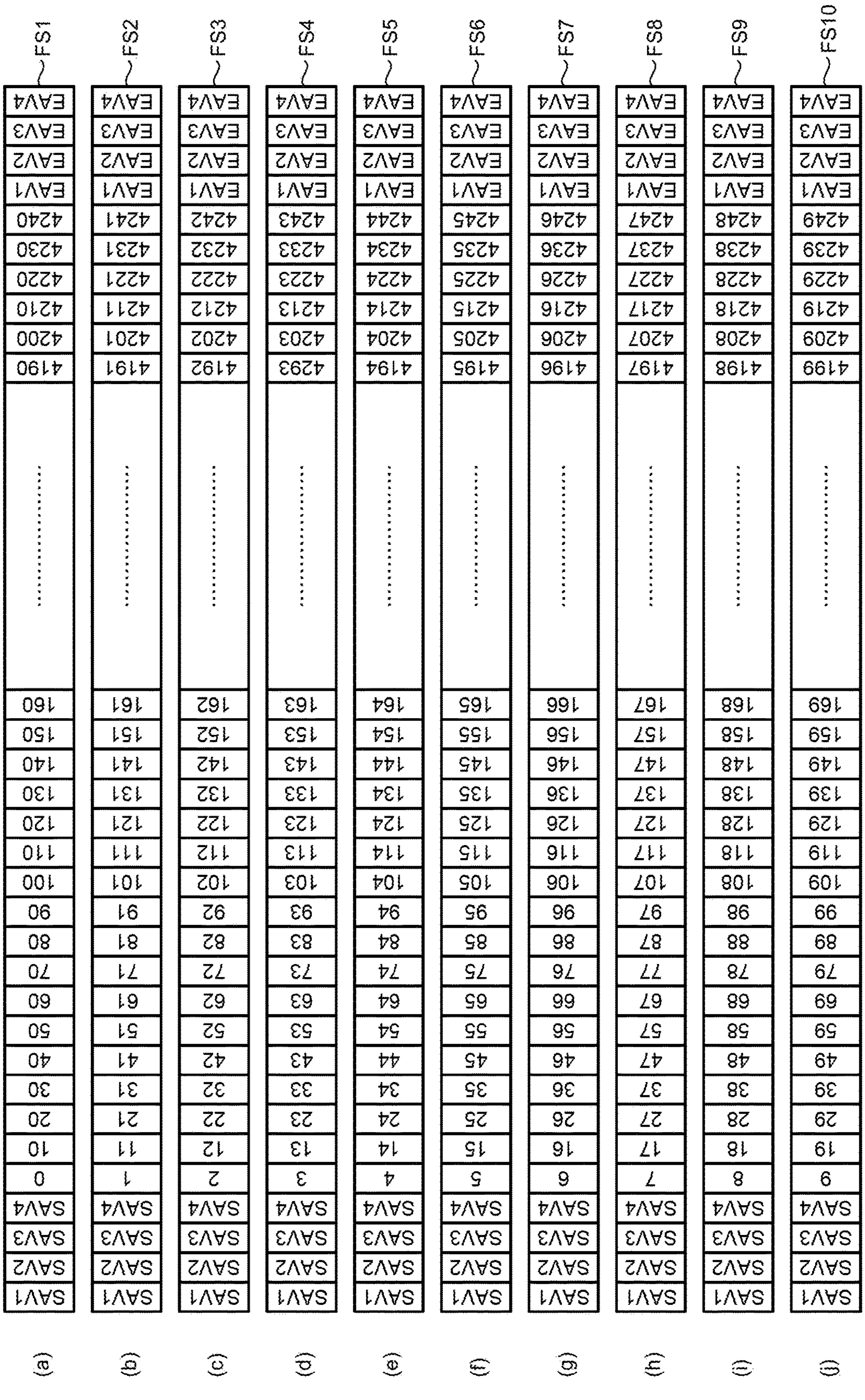
FIG. 5 is a diagram illustrating first to tenth image signals after S/P conversion processing is executed at an S/P conversion unit illustrated in FIG. 4.

Although not illustrated in FIGS. 3A and 3B, the imaging unit 223 outputs timing reference codes "SAV1" to "SAV4" made of four words (one word=10 bits) in parallel through the first to the tenth channels CA to CJ (refer to FIG. 5)

before outputting, in parallel through the first to the tenth channels CA to CJ, pieces of pixel data (serial data) generated at 10 pixels each in an order of the address number. After outputting, in parallel through the first to the tenth channels CA to CJ, the pieces of pixel data (serial data) generated at 10 pixels each in an order of the address number, the imaging unit 223 outputs timing reference codes "EAV1" to "EAV4" made of four words (one word=10 bits) in parallel through the first to the tenth channels CA to CJ (refer to FIG. 5).

Figure 4:
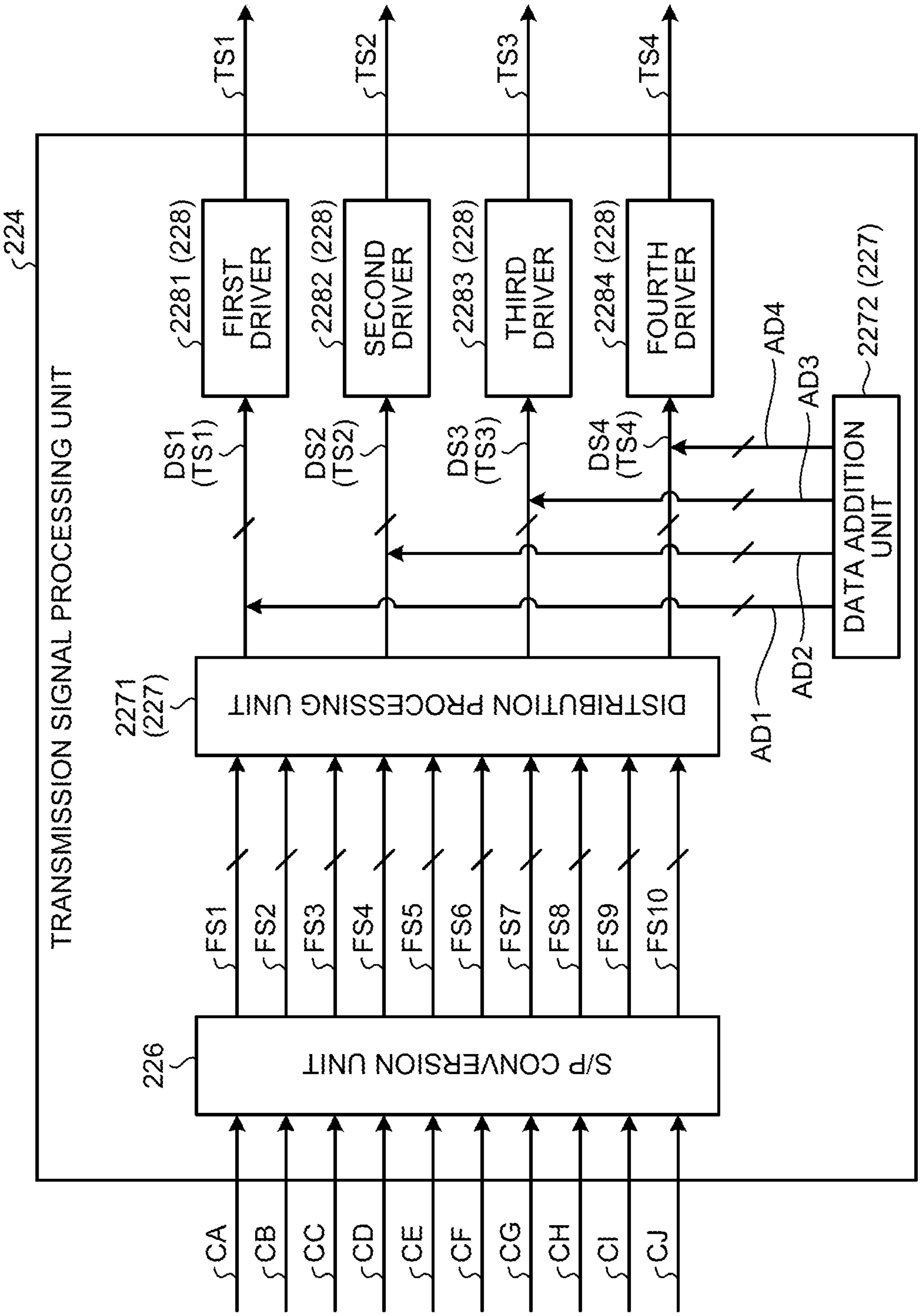
FIG. 4 is a block diagram of the configuration of a transmission signal processing unit illustrated in FIG. 2.

FIG. 4 is a block diagram of the configuration of the transmission signal processing unit 224.

In FIG. 4, the flow of a signal output in parallel data is illustrated by an arrow intersected with a diagonal line. The same notation applies to FIG. 2 and the following figures.

The transmission signal processing unit 224 functions as a medical signal processing device according to the present disclosure and executes, on the image signal (in 10 bits through 10 channels) from the imaging unit 223, various kinds of processing such as S/P conversion processing, transmission image signal generation processing (mapping processing and auxiliary data addition processing), encoding processing (N bit/M (>N) bit conversion processing (in the first embodiment, 8 bits/10 bits conversion processing)), and P/S conversion processing. As illustrated in FIG. 4, the transmission signal processing unit 224 includes an S/P conversion unit 226, a signal processing unit 227, and a plurality of drivers 228.

The S/P conversion unit 226 executes the S/P conversion processing on the image signal (serial data in 10 bits through 10 channels) output from the imaging unit 223 and converts the image signal into parallel data.

FIG. 5 is a diagram illustrating first to tenth image signals FS1 to FS10 (parallel data) after the S/P conversion processing is executed at the S/P conversion unit 226.

Numbers ("0" to "4249") illustrated in FIG. 5 correspond to the address numbers illustrated in FIG. 3A and each indicate pixel data (10 bits) generated at a pixel of the corresponding address number. Pixel data generated at the pixels of address numbers "0" to "4249" is effective data (pixel data obtained in an effective image region).

Specifically, as illustrated in (a) in FIG. 5, the S/P conversion unit 226 generates the first image signal FS1 (parallel data) by executing the S/P conversion processing on an image signal (the timing reference codes "SAV1" to "SAV4" and "EAV1" to "EAV4", and pieces of pixel data (pieces of pixel data generated at the pixels of address numbers "0", "10", "20", . . . )) output through the first channel CA. As illustrated in (b) in FIG. 5, the S/P conversion unit 226 also generates the second image signal FS2 (parallel data) by executing the S/P conversion processing on an image signal (the timing reference codes "SAV1" to "SAV4" and "EAV1" to "EAV4", and pieces of pixel data (pieces of pixel data generated at the pixels of address numbers "1", "11", "21", . . . )) output through the second channel CB. Similarly, as illustrated in (c) to (j) in FIG. 5, the S/P conversion unit 226 generates the third to the tenth image signals FS3 to FS10 (parallel data) by executing the S/P conversion processing on image signals output through the third to the tenth channels CC to CJ.

In the first embodiment, address numbers of "0" to "4249" are provided and thus the number of pixels in the effective image region of the image sensor 2231 is 4250, but the present disclosure is not limited thereto. The number of pixels in the effective image region of an image sensor in use may be changed to any other number as appropriate.

The signal processing unit 227 generates a plurality of transmission image signals by executing the transmission signal generation processing (the mapping processing and the auxiliary data addition processing) on the first to the tenth image signals FS1 to FS10 (parallel data) generated at the S/P conversion unit 226.

In the first embodiment, as illustrated in FIG. 4, the signal processing unit 227 generates four of first to fourth transmission image signals TS1 to TS4 from the first to the tenth image signals FS1 to FS10. The number of transmission image signals is not limited to four but may be any other number.

As illustrated in FIG. 4, the signal processing unit 227 includes a distribution processing unit 2271 and a data addition unit 2272.

The distribution processing unit 2271 generates four of first to fourth distributed image signals DS1 to DS4 by distributing (executes the mapping processing on) the first to the tenth image signals FS1 to FS10 (parallel data) generated at the S/P conversion unit 226.

Figure 6:
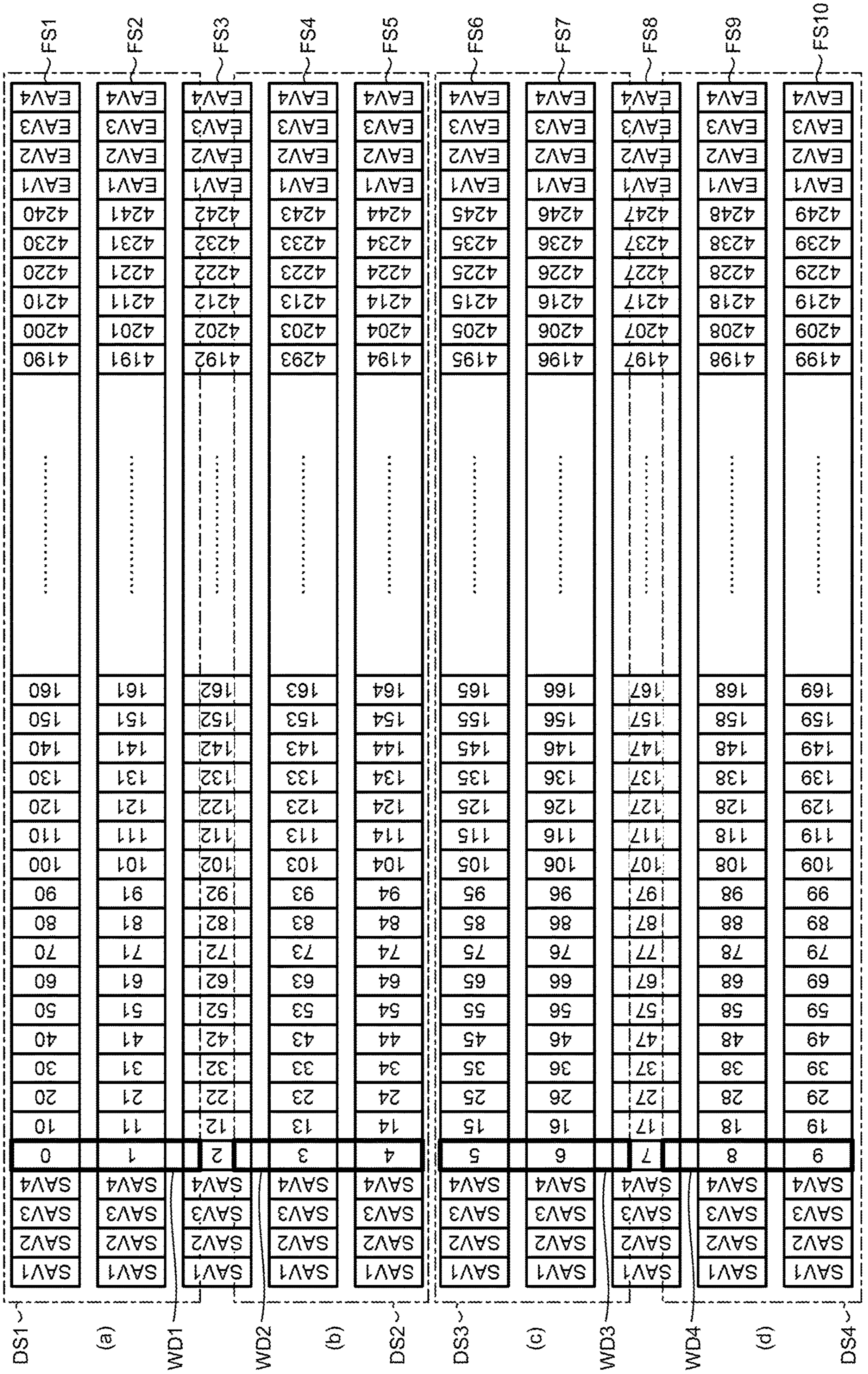
FIG. 6 is a diagram illustrating first to fourth distributed image signals generated at a distribution processing unit illustrated in FIG. 4.
Figure 7:
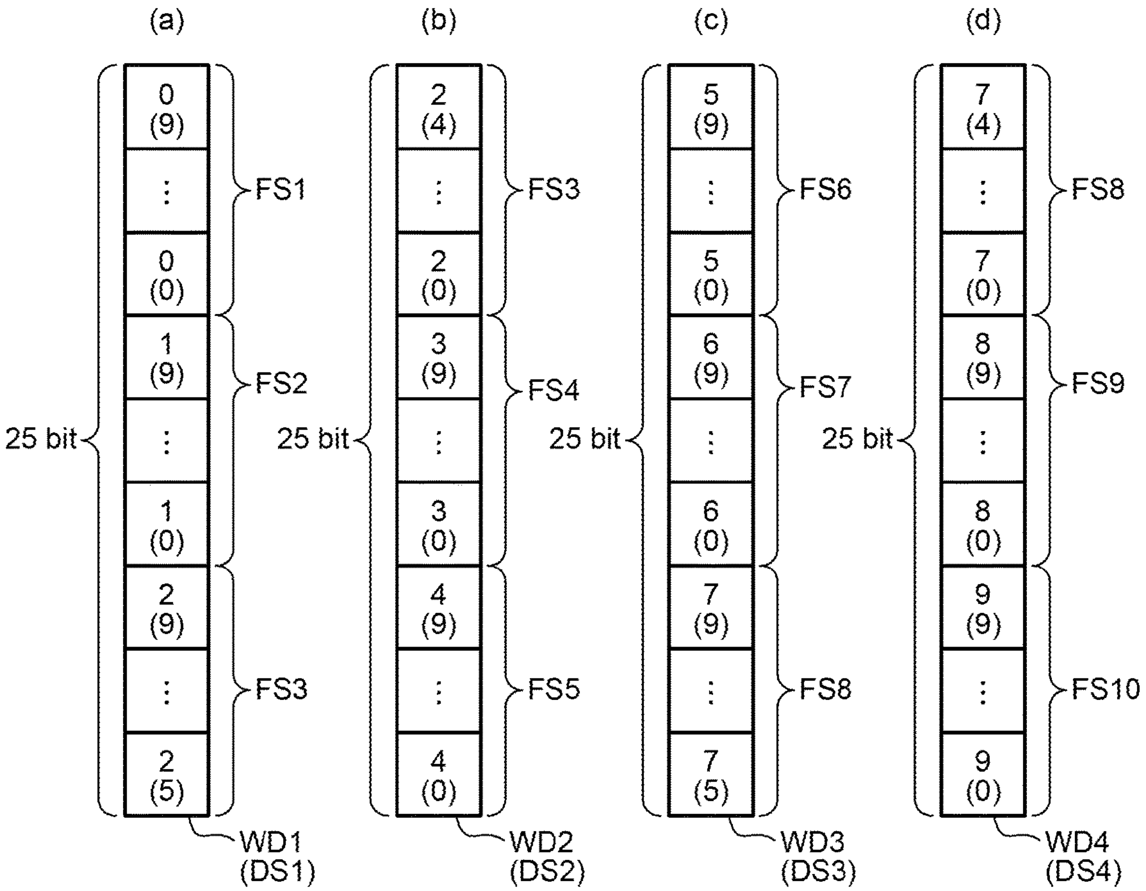
FIG. 7 is a diagram illustrating the first to the fourth distributed image signals generated at the distribution processing unit illustrated in FIG. 4.

FIGS. 6 and 7 are diagrams illustrating the first to the fourth distributed image signals DS1 to DS4 generated at the distribution processing unit 2271. Specifically, FIG. 6 corresponds to FIG. 5. (a) to (d) in FIG. 7 illustrate bit strings of the words WD1 to WD4 illustrated in (a) to (d) in FIG. 6, respectively.

In (a) to (d) in FIG. 7, each bit in the words WD1 to WD4 is denoted by an address number indicating the pixel of the corresponding pixel data, followed by a bit position in this pixel data in parentheses.

Specifically, as illustrated in FIGS. 6 and 7, the distribution processing unit 2271 distributes the first to the tenth image signals FS1 to FS10 (in 10 bits through 10 channels) into four signals (in 25 bits through four channels) so that the amount of data per word is constant between the first to the fourth distributed image signals DS1 to DS4. Specifically, as illustrated in (a) in FIG. 6 and (a) in FIG. 7, the first distributed image signal DS1 is a combination of the first image signal FS1 (10 bits), the second image signal FS2 (10 bits), and an image signal of the most significant five bits of the third image signal FS3 (10 bits). As illustrated in (b) in FIG. 6 and (b) in FIG. 7, the second distributed image signal DS2 is a combination of an image signal of the least significant five bits of the third image signal FS3 (10 bits), the fourth image signal FS4 (10 bits), and the fifth image signal FS5 (10 bits). As illustrated in (c) in FIG. 6 and (c) in FIG. 7, the third distributed image signal DS3 is a combination of the sixth image signal FS6 (10 bits), the seventh image signal FS7 (10 bits), and an image signal of the most significant five bits of the eighth image signal FS8 (10 bits). As illustrated in (d) in FIG. 6 and (d) in FIG. 7, the fourth distributed image signal DS4 is a combination of an image signal of the least significant five bits of the eighth image signal FS8 (10 bits), the ninth image signal FS9 (10 bits), and the tenth image signal FS10 (10 bits).

The data addition unit 2272 generates the first to the fourth transmission image signals TS1 to TS4 by adding, as auxiliary data to at least any of the four of the first to the fourth distributed image signals DS1 to DS4, data of at least part of distributed image signals different from the distributed image signal (by executing the auxiliary data addition processing).

In the first embodiment, the data addition unit 2272 adds, as auxiliary data to each of the four of the first to the fourth distributed image signals DS1 to DS4, at least data of the MSB of each pixel data included in another distributed image signal. The data addition unit 2272 adds 7-bit auxiliary data to each of the four of the first to the fourth distributed image signals DS1 to DS4 (25 bits) to enable execution of the 8 bits/10 bits conversion processing at a later stage. The auxiliary data is not limited to 7-bit data but may be data in any other number of bits.

The following describes the auxiliary data added at the data addition unit 2272 with reference to exemplary auxiliary data added to each of the words WD1 to WD4 illustrated in FIGS. 6 and 7.

Figure 8:
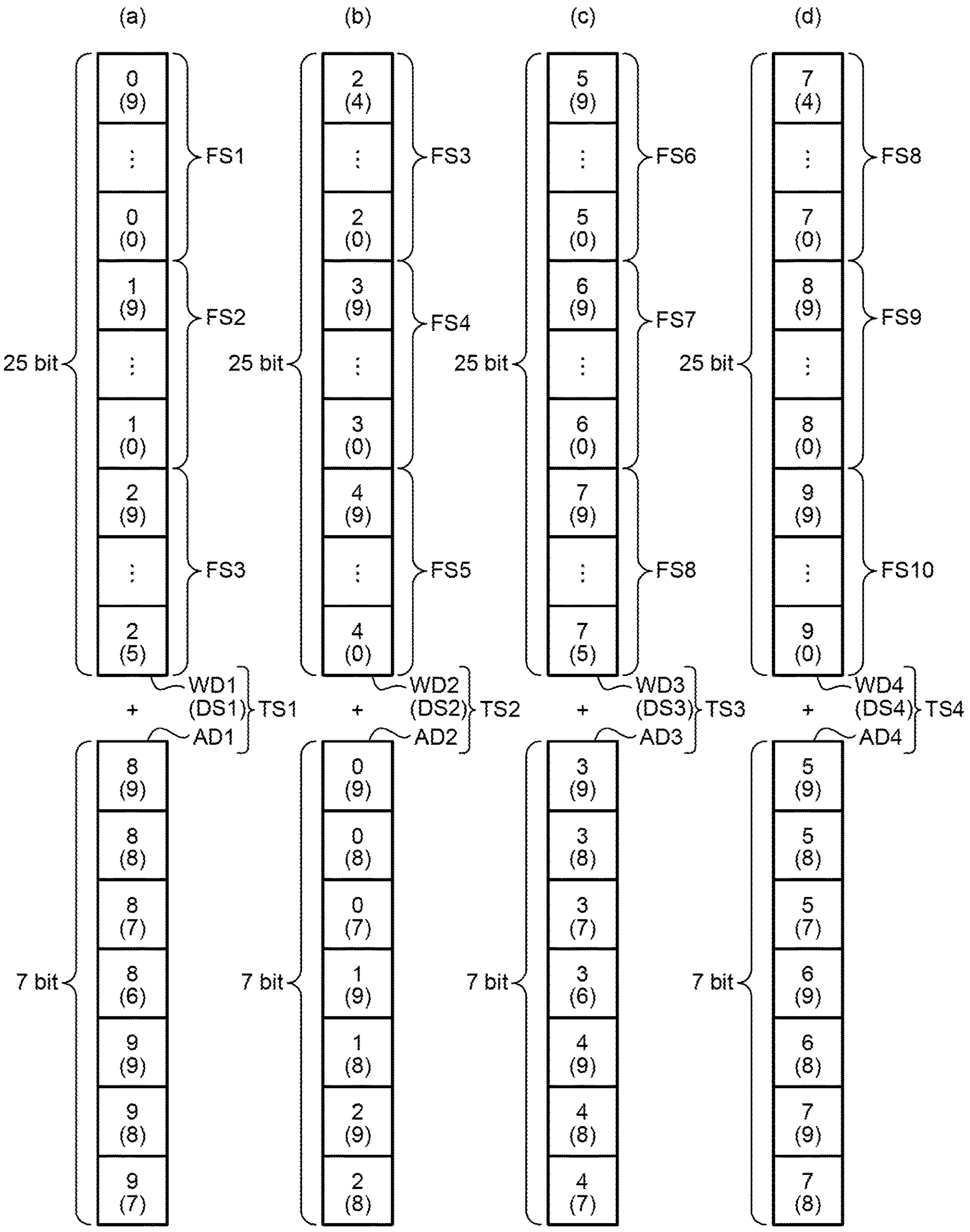
FIG. 8 is a diagram illustrating first to the fourth auxiliary data added at a data addition unit illustrated in FIG. 4.

FIG. 8 is a diagram illustrating first to fourth auxiliary data AD1 to AD4 added at the data addition unit 2272.

(a) to (d) in FIG. 8 illustrate the words WD1 to WD4 illustrated in FIGS. 6 and 7 and the first to the fourth auxiliary data AD1 to AD4 added to the words WD1 to WD4. In (a) to (d) in FIG. 8, each bit in the first to the fourth auxiliary data AD1 to AD4 is denoted by an address number indicating a pixel of the corresponding pixel data, followed by a bit position in this pixel data in parentheses.

Specifically, the data addition unit 2272 adds at least data of the MSB of each pixel data included in the fourth distributed image signal DS4 as the first auxiliary data AD1 to the first distributed image signal DS1. Specifically, as illustrated in (a) in FIG. 8, the first auxiliary data AD1 added to the word WD1 (first distributed image signal DS1) includes data of the MSB of pixel data generated at the pixel of address number "8" in the fourth distributed image signal DS4, data of the MSB of pixel data generated at the pixel of address number "9" in the fourth distributed image signal DS4, and other data (5 bits). The data addition unit 2272 also adds at least data of the MSB of each pixel data included in the first distributed image signal DS1 as the second auxiliary data AD2 to the second distributed image signal DS2. Specifically, as illustrated in (b) in FIG. 8, the second auxiliary data AD2 added to the word WD2 (second distributed image signal DS2) includes data of the MSB of pixel data generated at the pixel of address number "0" in the first distributed image signal DS1, data of the MSB of pixel data generated at the pixel of address number "1" in the first distributed image signal DS1, and data of the MSB of pixel data generated at the pixel of address number "2" in the first distributed image signal DS1, and other data (4 bits). The data addition unit 2272 also adds at least data of the MSB of each pixel data included in the second distributed image signal DS2 as the third auxiliary data AD3 to the third distributed image signal DS3. Specifically, as illustrated in (c) in FIG. 8, the third auxiliary data AD3 added to the word WD3 (third distributed image signal DS3) includes data of the MSB of pixel data generated at the pixel of address number "3" in the second distributed image signal DS2, data of the MSB of pixel data generated at the pixel of address number "4" in the second distributed image signal DS2, and other data (5 bits). The data addition unit 2272 also adds at least data of the MSB of each pixel data included in the third distributed image signal DS3 as the fourth auxiliary data AD4 to the fourth distributed image signal DS4. Specifically, as illustrated in (d) in FIG. 8, the fourth auxiliary data AD4 added to the word WD4 (fourth distributed image signal DS4) includes data of the MSB of pixel data generated at the pixel of address number "5" in the third distributed image signal DS3, data of the MSB of pixel data generated at the pixel of address number "6" in the third distributed image signal DS3, data of the MSB of pixel data generated at the pixel of address number "7" in the third distributed image signal DS3, and other data (4 bits).

Other data that is described above and included in the first to the fourth auxiliary data AD1 to AD4 (data other than the MSB data) may be any data. In the first embodiment, as illustrated in (a) in FIG. 8, the other data in the first auxiliary data AD1 includes data at bit positions "8" to "6" in pixel data generated at the pixel of address number "8", and data at bit positions "8" and "7" in pixel data generated at the pixel of address number "9". As illustrated in (b) in FIG. 8, the other data in the second auxiliary data AD2 includes data at bit positions "8" and "7" in pixel data generated at the pixel of address number "0", data at bit position "8" in pixel data generated at the pixel of address number "1", and data at bit position "8" in pixel data generated at the pixel of address number "2". As illustrated in (c) in FIG. 8, the other data in the third auxiliary data AD3 includes data at bit positions "8" to "6" in pixel data generated at the pixel of address number "3", and data at bit positions "8" and "7" in pixel data generated at the pixel of address number "4". As illustrated in (d) in FIG. 8, the other data in the fourth auxiliary data AD4 includes data at bit positions "8" and "7" in pixel data generated at the pixel of address number "5", data at bit position "8" in pixel data generated at the pixel of address number "6", and data at bit position "8" in pixel data generated at the pixel of address number "7".

The drivers 228 are provided in accordance with the number of transmission image signals generated at the signal processing unit 227. Specifically, in the first embodiment, as illustrated in FIG. 4, the four drivers 228 of first to fourth drivers 2281 to 2284 are provided. The four of the first to the fourth drivers 2281 to 2284 execute the encoding processing (in the first embodiment, the 8 bits/10 bits conversion processing) on the first to the fourth transmission image signals TS1 to TS4 generated at the signal processing unit 227. The four of the first to the fourth drivers 2281 to 2284 execute the P/S conversion processing on the first to the fourth transmission image signals TS1 to TS4 after the encoding processing to convert the signals into serial data. Although not specifically illustrated, a clock signal is superimposed on this serial data, and, for example, a K code indicating the start position and the end position of effective data is inserted into the serial data.

The transmission signal processing unit 224 described above is achieved by a programmable logic device such as a field-programmable gate array (FPGA).

The electrical-optical conversion unit 225 converts the first to the fourth transmission image signals TS1 to TS4 (serial data) output from the transmission signal processing unit 224 (the four of the first to the fourth drivers 2281 to 2284) into optical signals, and outputs the optical signals to the first transmission cable 23 (the first to the fourth optical fibers 2321 to 2324). Then, the first to the fourth optical fibers 2321 to 2324 transmit the first to the fourth transmission image signals TS1 to TS4 to the control device 6.

Configuration of Control Device

The following describes the configuration of the control device 6 with reference to FIG. 2.

As illustrated in FIG. 2, the control device 6 includes an optical-electrical conversion unit 61, a received signal processing unit 62, an image processing unit 63, a display control unit 64, a control unit 65, an input unit 66, an output unit 67, and a storage unit 68.

The optical-electrical conversion unit 61 converts the four optical signals (the four of the first to the fourth transmission image signals TS1 to TS4) received through the first to the fourth optical fibers 2321 to 2324 into electric signals (serial data).

Figure 9:
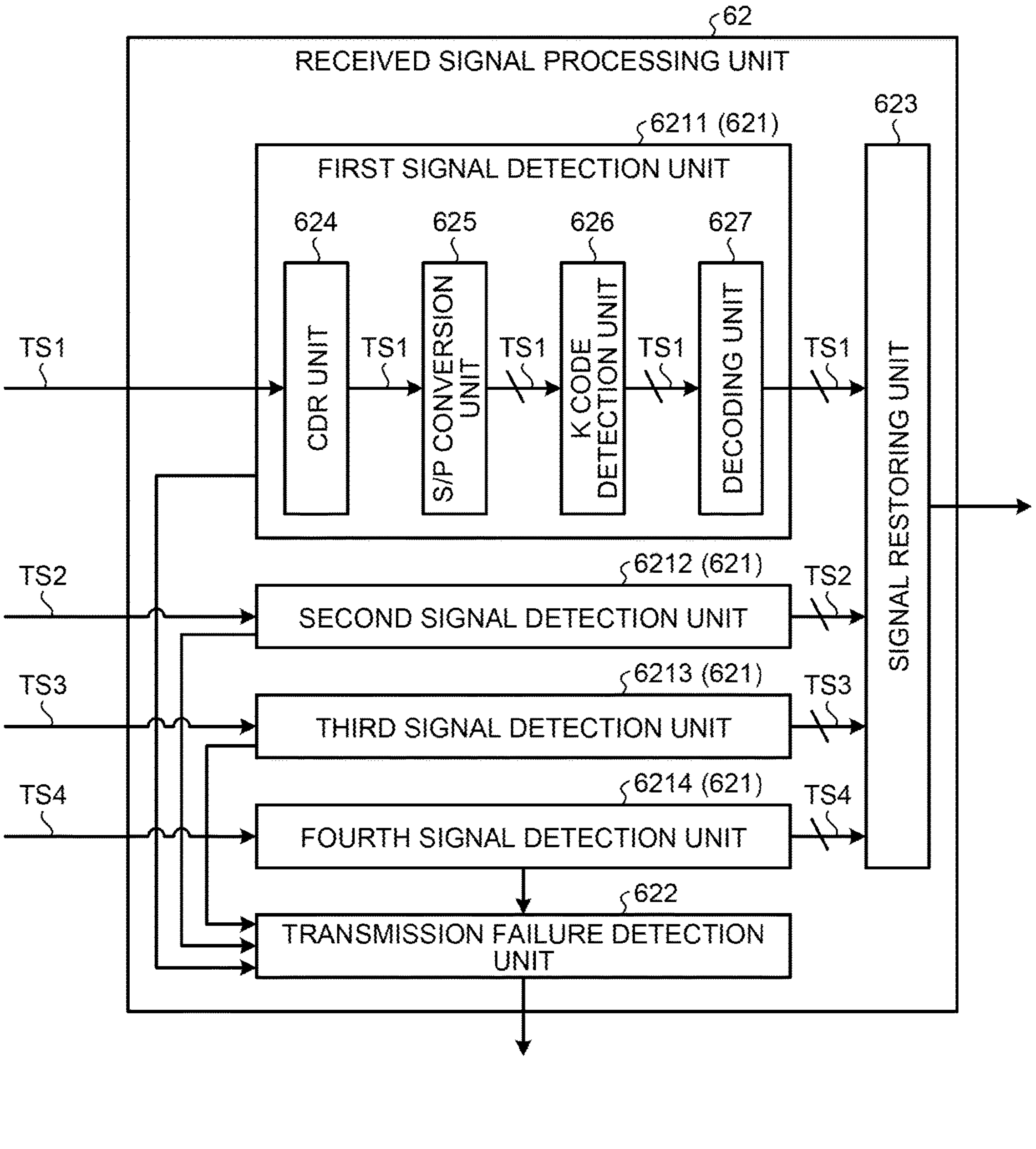
FIG. 9 is a block diagram of the configuration of a received signal processing unit illustrated in FIG. 2.

FIG. 9 is a block diagram of the configuration of the received signal processing unit 62.

The received signal processing unit 62 functions as a medical control device according to the present disclosure and executes, on the four pieces of serial data (the four of the first to the fourth transmission image signals TS1 to TS4) output from the optical-electrical conversion unit 61, various kinds of processing such as transmission failure detection processing, the S/P conversion processing, decoding processing (M bit/N (<M) bit conversion processing (in the first embodiment, 10 bits/8 bits conversion processing)), mapping decoding processing, and the P/S conversion processing. As illustrated in FIG. 9, the received signal processing unit 62 includes a plurality of signal detection units 621, a transmission failure detection unit 622, and a signal restoring unit 623.

The signal detection units 621 are provided in accordance with the number of optical fibers 232 (the first to the fourth transmission image signals TS1 to TS4) included in the first transmission cable 23. Specifically, in the first embodiment, the four signal detection units 621 are provided. Hereinafter, the signal detection units 621 corresponding to the first to the fourth transmission image signals TS1 to TS4 are referred to as first to fourth signal detection units 6211 to 6214, respectively (FIG. 9). The first to the fourth signal detection units 6211 to 6214 have an identical configuration, and thus only the configuration of the first signal detection unit 6211 corresponding to the first transmission image signal TS1 will be described below. For the purpose of description, FIG. 9 only illustrates a specific configuration of the first signal detection unit 6211, whereas specific configurations of the second to the fourth signal detection units 6212 to 6214 are omitted in the illustration.

As illustrated in FIG. 9, the first signal detection unit 6211 includes a clock recovery (CDR) unit 624, an S/P conversion unit 625, a K code detection unit 626, and a decoding unit 627.

The CDR unit 624 executes CDR processing that recovers the superimposed clock signal from the first transmission image signal TS1 (serial data) input to the optical-electrical conversion unit 61 through the optical fiber 232 (first optical fiber 2321) and converted at the optical-electrical conversion unit 61. Then, when the execution of the CDR processing is successful (the recovery of the superimposed clock signal is successful), the CDR unit 624 outputs processing execution information indicating the successful execution to the transmission failure detection unit 622. When the execution of the CDR processing is failed, the CDR unit 624 outputs, to the transmission failure detection unit 622, failed execution information indicating the failure, and identification information for identifying the optical fiber 232 (first optical fiber 2321) corresponding to the CDR unit 624.

The S/P conversion unit 625 executes the S/P conversion processing on the first transmission image signal TS1 (serial data) after the CDR processing to convert the signal into parallel data.

The K code detection unit 626 detects the K code from the first transmission image signal TS1 (parallel data) after the S/P conversion processing at the S/P conversion unit 625 to perform timing detection of data, and executes K code detection processing that acquires the effective data from the first transmission image signal TS1 (parallel data). Then, when the execution of the K code detection processing is successful (the acquisition of the effective data is successful), the K code detection unit 626 outputs processing execution information indicating the successful execution to the transmission failure detection unit 622. When the execution of the K code detection processing is failed, the K code detection unit 626 outputs, to the transmission failure detection unit 622, failed execution information indicating the failure, and identification information for identifying the optical fiber 232 (first optical fiber 2321) corresponding to the K code detection unit 626.

In the first embodiment, the K code detection unit 626 is employed, but the present disclosure is not limited thereto. When information other than the K code is inserted into the first to the fourth transmission image signals TS1 to TS4 by the camera head 22, a component having a function of detecting this information (component that outputs, to the transmission failure detection unit 622, for example, whether this information may be detected) may be employed.

The decoding unit 627 executes the decoding processing (in the first embodiment, 10 bits/8 bits conversion processing) on the first transmission image signal TS1 (effective data (parallel data) acquired at the K code detection unit 626) after the K code detection processing at the K code detection unit 626.

The transmission failure detection unit 622 detects any failure of transmission of optical signals through the first to the fourth optical fibers 2321 to 2324 based on the information output from the first to the fourth signal detection units 6211 to 6214 (the CDR unit 624 and the K code detection unit 626), and specifies an optical fiber in which a transmission failure has occurred.

Specifically, the first to the fourth signal detection units 6211 to 6214 and the transmission failure detection unit 622 execute the transmission failure detection processing to detect any failure of transmission of optical signals through the first to the fourth optical fibers 2321 to 2324, and specifies an optical fiber in which the transmission failure has occurred.

Then, the transmission failure detection unit 622 outputs transmission failure information (information indicating whether a transmission failure has occurred, and when a transmission failure occurs, an optical fiber in which this transmission failure has occurred) to the control unit 65.

The signal restoring unit 623 restores image signals (the first to the tenth image signals FS1 to FS10 (parallel data)) before the mapping processing at the camera head 22 by executing the mapping decoding processing on the first to the fourth transmission image signals TS1 to TS4 (parallel data) after the decoding processing at the decoding units 627 in the first to the fourth signal detection units 6211 to 6214. Then, the signal restoring unit 623 executes the P/S conversion processing on the restored image signals (parallel data) to convert the signals into serial data.

The signal restoring unit 623 executes different mapping decoding processing depending on whether a transmission failure is detected by the transmission failure detection unit 622.

The following first describes the mapping decoding processing when no transmission failure is detected.

The signal restoring unit 623 extracts the first to the fourth distributed image signals DS1 to DS4, respectively, from the first to the fourth transmission image signals TS1 to TS4 after the decoding processing at each of the decoding units 627 in the first to the fourth signal detection units 6211 to 6214. Then, the signal restoring unit 623 combines the extracted first to fourth distributed image signals DS1 to DS4 to restore the image signals before the mapping processing at the camera head 22.

The mapping decoding processing when a transmission failure is detected will be described next.

For example, when the optical fiber (optical fiber in which a transmission failure has occurred) specified at the transmission failure detection unit 622 is the first optical fiber 2321 only, the control device 6 is unable to favorably receive the first transmission image signal TS1 through the first optical fiber 2321. In other words, the signal restoring unit 623 is unable to favorably extract the first distributed image signal DS1 from the first transmission image signal TS1. Accordingly, the signal restoring unit 623 is unable to restore the image signals before the mapping processing at the camera head 22 by combining the first to the fourth distributed image signals DS1 to DS4.

To solve this problem, the signal restoring unit 623 uses the second auxiliary data AD2 ((b) in FIG. 8) included in the second transmission image signal TS2 transmitted through the second optical fiber 2322. As described above, the second auxiliary data AD2 includes at least data of the MSB of each pixel data included in the first distributed image signal DS1. Thus, the signal restoring unit 623 restores the first distributed image signal DS1 by using the second auxiliary data AD2. Then, the signal restoring unit 623 restores the image signals before the mapping processing at the camera head 22 by combining the restored first distributed image signal DS1 and the second to the fourth distributed image signals DS2 to DS4 extracted from the second to the fourth transmission image signal TS2 to TS4 after the decoding processing at each of the decoding units 627 in the second to the fourth signal detection units 6212 to 6214.

Similarly, when a transmission failure occurs in any one of the second to the fourth optical fibers 2322 to 2324, the signal restoring unit 623 restores the image signals before the mapping processing at the camera head 22.

Specifically, at least data of the MSB of each pixel data included in the fourth distributed image signal DS4 is added as the first auxiliary data AD1 to the first distributed image signal DS1. At least data of the MSB of each pixel data included in the second distributed image signal DS2 is added as the third auxiliary data AD3 to the third distributed image signal DS3. At least data of the MSB of each pixel data included in the third distributed image signal DS3 is added as the fourth auxiliary data AD4 to the fourth distributed image signal DS4. Thus, when a transmission failure occurs in any one of the second to the fourth optical fibers 2322 to 2324, the signal restoring unit 623 restores a distributed image signal corresponding to the optical fiber in which a transmission failure has occurred by using a transmission image signal (auxiliary data) transmitted through an optical fiber in which no transmission failure has occurred.

The amount of data at each bit position of pixel data included in the first to the fourth distributed image signals DS1 to DS4 is as follows.

Figure 10:
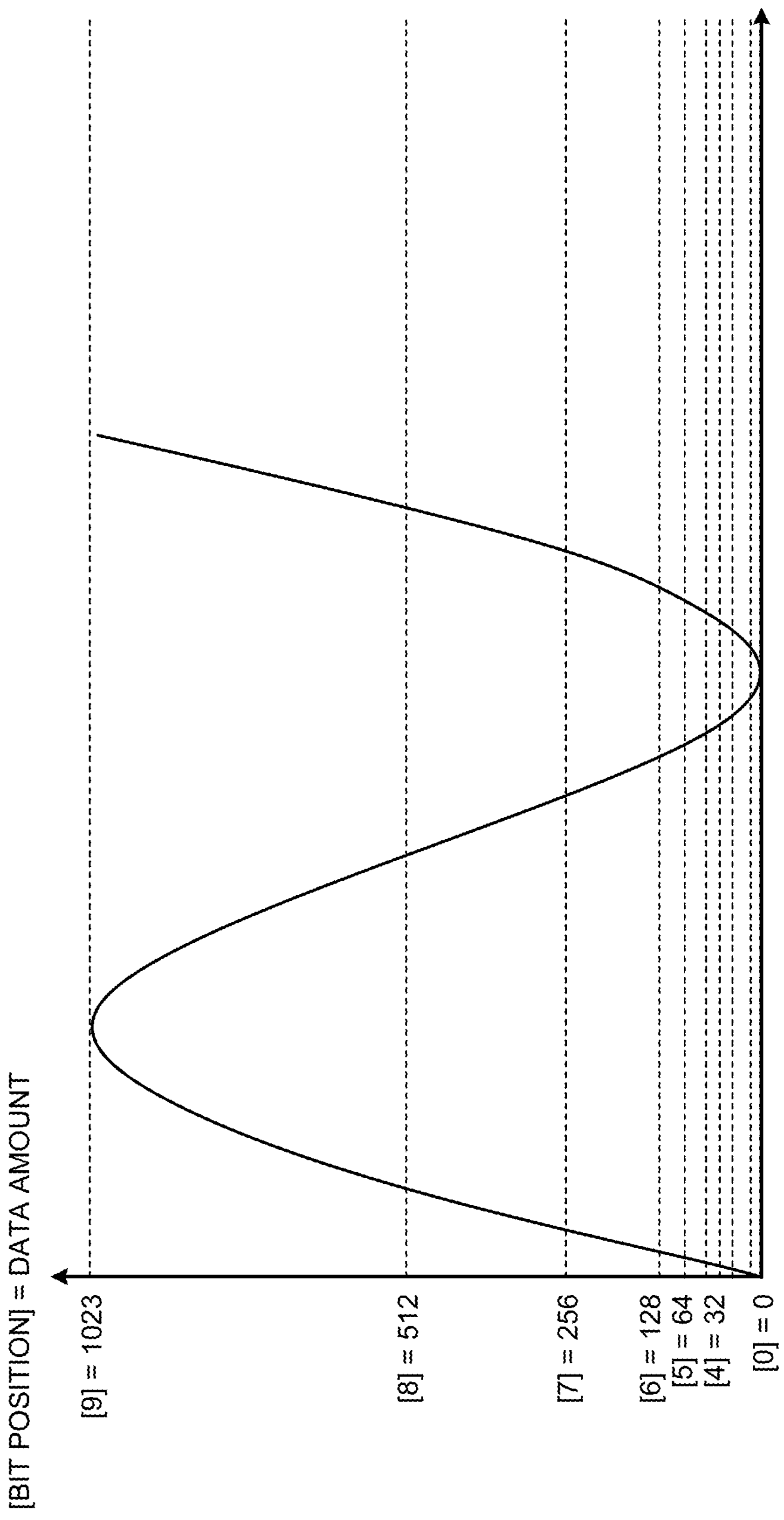
FIG. 10 is a diagram illustrating the amount of data at each bit position in 10-bit pixel data.

FIG. 10 is a diagram illustrating the amount of data at each bit position in 10-bit pixel data.

Specifically, in 10-bit pixel data, as illustrated in FIG. 10, the amount of data at the bit position of the MSB accounts for half of the amount of the entire pixel data. The amount of data at bit position "8" accounts for a quarter of the amount of the entire pixel data. In other words, data at the bit position of a more significant digit is important data in pixel data.

Thus, when the first to the fourth auxiliary data AD1 to AD4 is set to be data including at least the MSB of each pixel data included in a distributed image signal to be restored, use of these first to fourth auxiliary data AD1 to AD4 in the mapping decoding processing described above enables excellent restoring of the distributed image signal.

Similarly to the transmission signal processing unit 224, the received signal processing unit 62 described above is achieved by a programmable logic device such as a FPGA.

The image processing unit 63 executes, on an image signal (serial data) restored at the received signal processing unit 62, various kinds of image processing such as development processing (demosaic processing), noise reduction, color correction, color enhancement, and outline enhancement.

The display control unit 64 generates a display image signal from the image signal (serial data) after the various kinds of image processing at the image processing unit 63, and outputs the display image signal to the display device 4 through the second transmission cable 5. Then, the display device 4 displays an image (hereinafter referred to as an observation image) based on this display image signal. When a transmission failure is detected by the transmission failure detection unit 622, the display control unit 64 generates an image signal for displaying, on the display device 4, a superimposed image obtained by superimposing, on the observation image, for example, a message indicating the occurrence of the transmission failure and a message indicating an optical fiber in which the transmission failure has occurred, and outputs the image signal to the display device 4 through the second transmission cable 5. Then, the display device 4 displays the superimposed image (image in which the messages are superimposed on the observation image) based on this image signal.

In other words, the display device 4 functions as a notification unit according to the present disclosure. The display control unit 64 functions as a notification control unit according to the present disclosure.

The control unit 65 includes, for example, a CPU, and controls operation of the light source device 3, the drive unit 222, the imaging unit 223, and the transmission signal processing unit 224 and operation of the entire control device 6 by outputting control signals through the third transmission cable 7 and the electric wires 231.

The input unit 66 includes an operation device such as a mouse, a keyboard, or a touch panel to receive an operation by a user.

The output unit 67 includes, for example, a speaker and a printer to output various kinds of information. When a transmission failure is detected by the transmission failure detection unit 622, the output unit 67 outputs sound indicating the occurrence of the transmission failure, and sound indicating an optical fiber in which the transmission failure has occurred.

In other words, the output unit 67 functions as the notification unit according to the present disclosure. The control unit 65 functions as the notification control unit according to the present disclosure.

The notification unit according to the present disclosure is not limited to the display device 4 and the output unit 67, but may be, for example, an LED that gives notification of predetermined information by lighting or flashing.

The medical observation system 1 according to the first embodiment described above achieves an effect described below.

Figure 11:
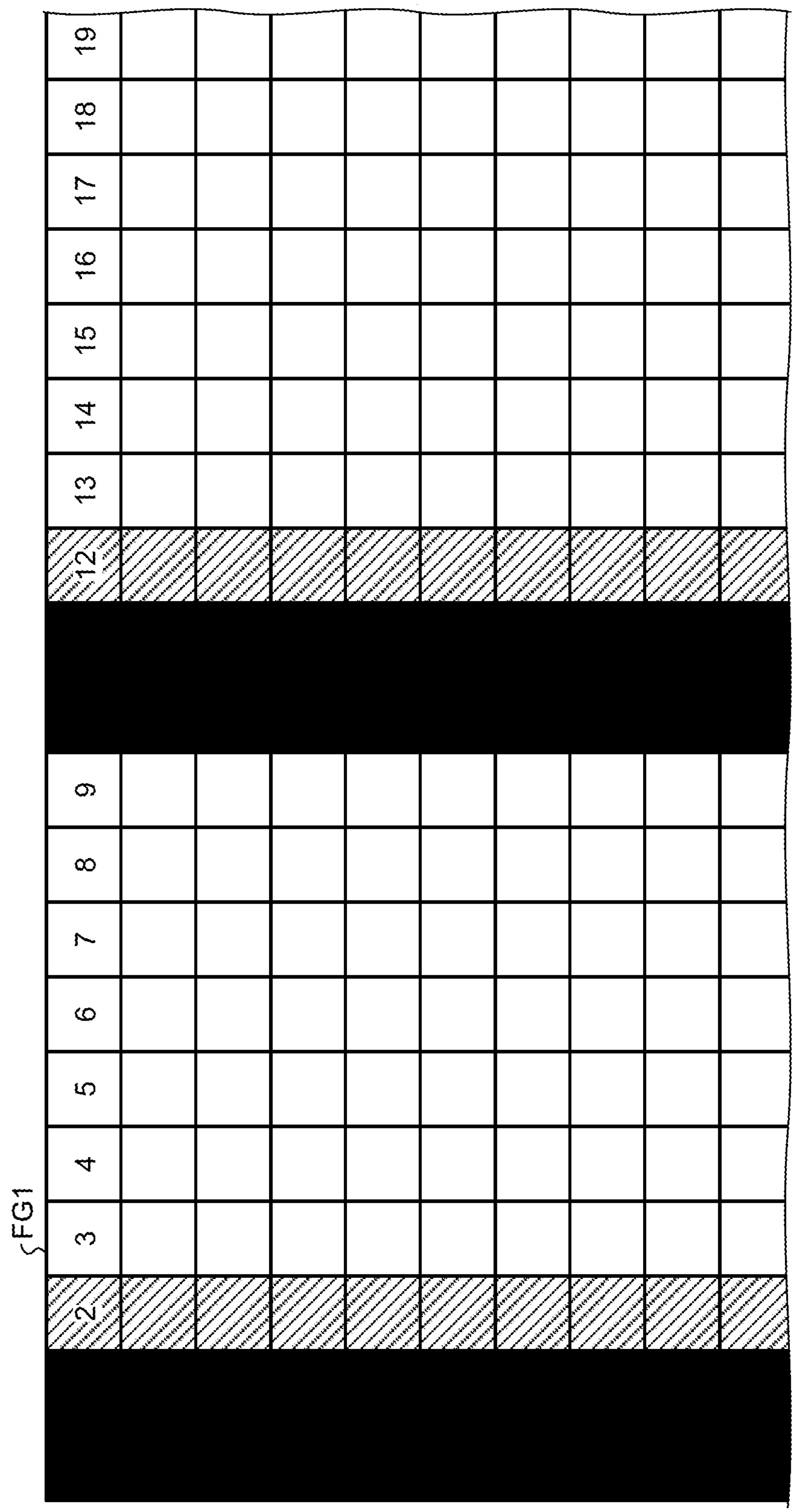
FIG. 11 is a diagram illustrating an effect of the first embodiment of the present disclosure.
Figure 12:
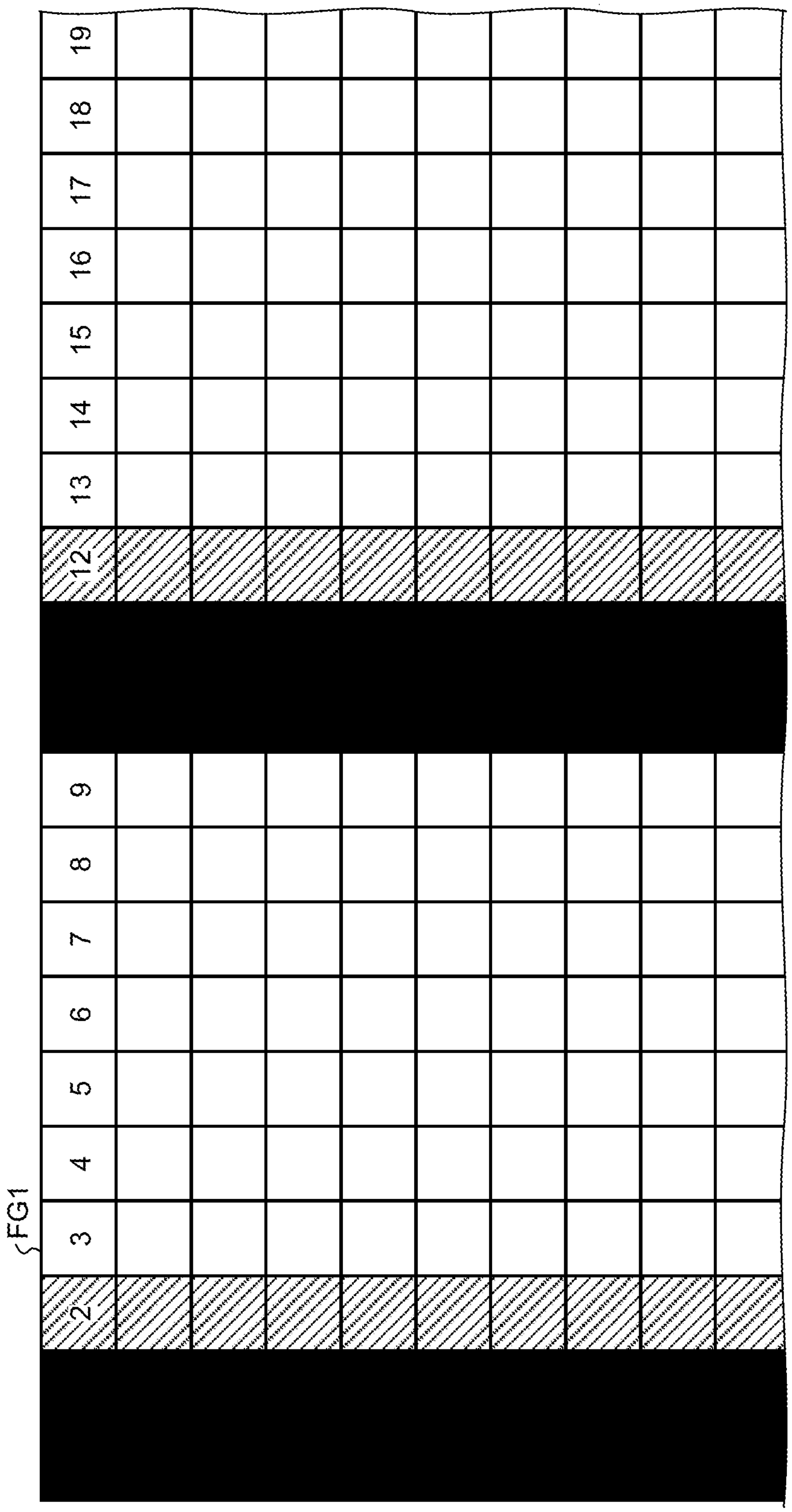
FIG. 12 is a diagram illustrating the effect of the first embodiment of the present disclosure.

FIGS. 11 and 12 are each a diagram illustrating the effect of the first embodiment of the present disclosure. Specifically, FIG. 11 is a diagram illustrating an observation image FG1 displayed on the display device 4 when a transmission failure occurs in the first optical fiber 2321, and illustrates a case in which the first distributed image signal DS1 is not restored by using the second auxiliary data AD2. FIG. 12 is a diagram illustrating an observation image FG2 displayed on the display device 4 when a transmission failure occurs in the first optical fiber 2321, and illustrates a case in which the first distributed image signal DS1 is restored by using the second auxiliary data AD2.

In FIGS. 11 and 12, for the purpose of description, the address number (FIG. 3A) corresponding to each pixel at the image sensor 2231 is attached to part of the observation images FG1 and FG2.

When a transmission failure occurs in the first optical fiber 2321 among the first to the fourth optical fibers 2321 to 2324, the control device 6 is unable to favorably receive the first transmission image signal TS1 through the first optical fiber 2321. In other words, the control device 6 is unable to favorably extract the first distributed image signal DS1 from the first transmission image signal TS1.

The first distributed image signal DS1 is a combination of the first image signal FS1 including pieces of pixel data generated at the pixels of address numbers “0”, “10”, “20”, . . . , the second image signal FS2 including pieces of pixel data generated at the pixels of address numbers “1”, “11”, “21”, . . . , and an image signal of the most significant five bits of the third image signal FS3 including pieces of pixel data generated at the pixels of address numbers “2”, “12”, “22”, . . . .

Thus, when a transmission failure occurs in the first optical fiber 2321, in the observation image FG1 displayed on the display device 4, an image loss occurs on vertical lines of the first column, the eleventh column, . . . (the pixels of address numbers “0”, “10”, “20”, . . . ) corresponding to the first image signal FS1 as illustrated in FIG. 11 along with a loss of the first image signal FS1. In addition, in the observation image FG1, an image loss occurs on vertical lines of the second column, the twelfth column, . . . (the pixels of address numbers “1”, “11”, “21”, . . . ) corresponding to the second image signal FS2 along with a loss of the second image signal FS2. In addition, in the observation image FG1, the luminance value is reduced on vertical lines of the third column, the thirteenth column, . . . (the pixels of address numbers “2”, “12”, “22”, . . . ) corresponding to the third image signal FS3 along with a loss of the image signal of the most significant five bits in the third image signal FS3.

In the medical observation system 1 according to the first embodiment, however, the transmission signal generation processing (auxiliary data addition processing) adds, as auxiliary data to each of the four of the first to the fourth distributed image signals DS1 to DS4, at least data of the MSB of each pixel data included in another distributed image signal. Specifically, the second auxiliary data AD2 added to the second distributed image signal DS2 includes at least data of the MSB of each pixel data included in the first distributed image signal DS1. With this configuration, the control device 6 restores the first distributed image signal DS1 by using the second auxiliary data AD2, and may appropriately generate a display image signal based on the restored first distributed image signal DS1 and the second to the fourth distributed image signals DS2 to DS4 extracted from the second to the fourth transmission image signal TS2 to TS4.

Thus, when a transmission failure occurs in the first optical fiber 2321, as illustrated in FIG. 12, the observation image FG2 displayed on the display device 4 does not suffer from the image loss on the vertical lines and the reduction of the luminance value in the observation image FG1 described above, and thus is an excellent image suitable for observation. The same description applies to when a transmission failure occurs in any one of the second to the fourth optical fibers 2322 to 2324.

In the medical observation system 1 according to the first embodiment, a distributed image signal corresponding to an optical fiber in which a transmission failure has occurred is restored by using auxiliary data as described above, and thus, when no transmission failure occurs, a simplified structure may be achieved without redundantly providing an unnecessary signal transmission path.

In the medical observation system 1 according to the first embodiment, the transmission signal generation processing (auxiliary data addition processing) adds, as auxiliary data to each of the four of the first to the fourth distributed image signals DS1 to DS4, at least data of the MSB of each pixel data included in another distributed image signal.

With this configuration, auxiliary data may only include data (at least data of the MSB) important for restoring a distributed image signal, and thus the amount of the auxiliary data may be reduced to a minimum amount.

The restoring of a distributed image signal may be more highly accurately performed with a larger amount of auxiliary data. Specifically, when the first to the tenth image signals FS1 to FS10 are distributed into four signals so that the amount of data per word is not constant between the first to the fourth distributed image signals DS1 to DS4, auxiliary data with a larger amount of data may be added to a distributed image signal with a smaller amount of data. With this configuration, a distributed image signal corresponding to an optical fiber in which a transmission failure has occurred may be more highly accurately restored by using such auxiliary data with a larger amount of data. However, it is difficult to predict in which of the first to the fourth optical fibers 2321 to 2324 a transmission failure will occurs. In other words, a distributed image signal corresponding to an optical fiber in which a transmission failure has occurred needs to be restored by using auxiliary data with a smaller amount of data in some cases.

In the medical observation system 1 according to the first embodiment, however, the first to the tenth image signals FS1 to FS10 are distributed into four signals through the mapping processing so that the amount of data per word is constant between the first to the fourth distributed image signals DS1 to DS4. Then, in the medical observation system 1, the first to the fourth auxiliary data AD1 to AD4 between which the amount of data is constant is added to the first to the fourth distributed image signals DS1 to DS4 through the auxiliary data addition processing.

With this configuration, when a transmission failure occurs in any one of the first to the fourth optical fibers 2321 to 2324, a distributed image signal corresponding to the optical fiber in which the transmission failure has occurred may be restored with an identical accuracy by using any one of the first to the fourth auxiliary data AD1 to AD4 between which the amount of data is constant.

In the medical observation system 1 according to the first embodiment, when a transmission failure is detected, notification of predetermined information (information indicating the occurrence of the transmission failure and an optical fiber in which the transmission failure has occurred) is given through the display device 4 and the output unit 67.

This configuration allows a user such as a doctor to recognize that an image (for example, the observation image FG2) displayed on the display device 4 is an image generated by restoring an image signal, and may suggest, to this user, replacement of the optical fiber in which the transmission failure has occurred.

Second Embodiment

The following describes a second embodiment of the present disclosure.

In the following description, any configuration identical to that of the first embodiment described above is denoted by an identical reference sign, and detailed description thereof will be omitted or simplified.

The medical observation system 1 according to the first embodiment described above is configured to deal with a case in which a transmission failure occurs in one of the first to the fourth optical fibers 2321 to 2324.

However, a medical observation system according to the second embodiment is configured to deal with a case in which transmission failures occur in a plurality (three at maximum) of optical fibers among the first to the fourth optical fibers 2321 to 2324, and is configured to execute the transmission signal generation processing (the mapping processing and the auxiliary data addition processing) and the mapping decoding processing different from those executed by the medical observation system 1 described in the first embodiment above.

Figure 13:
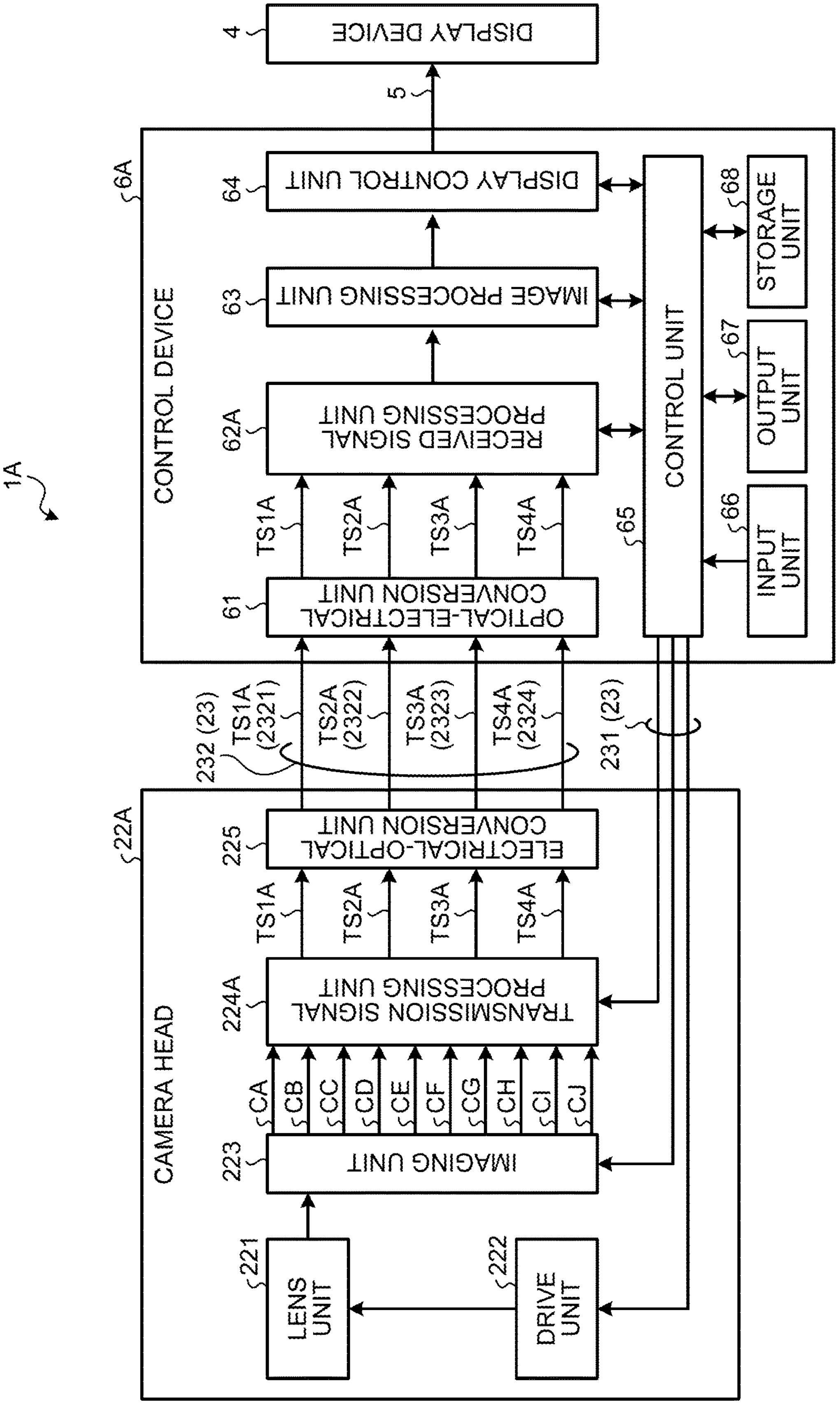
FIG. 13 is a block diagram of the configurations of a camera head and a control device in a medical observation system according to a second embodiment of the present disclosure.

FIG. 13 is a block diagram of the configurations of a camera head 22A and a control device 6A in a medical observation system 1A according to the second embodiment of the present disclosure.

Specifically, as illustrated in FIG. 13, the medical observation system 1A according to the second embodiment includes a transmission signal processing unit 224A and a received signal processing unit 62A in place of the transmission signal processing unit 224 and the received signal processing unit 62 of the medical observation system 1 described in the first embodiment above (FIG. 2).

Figure 14:
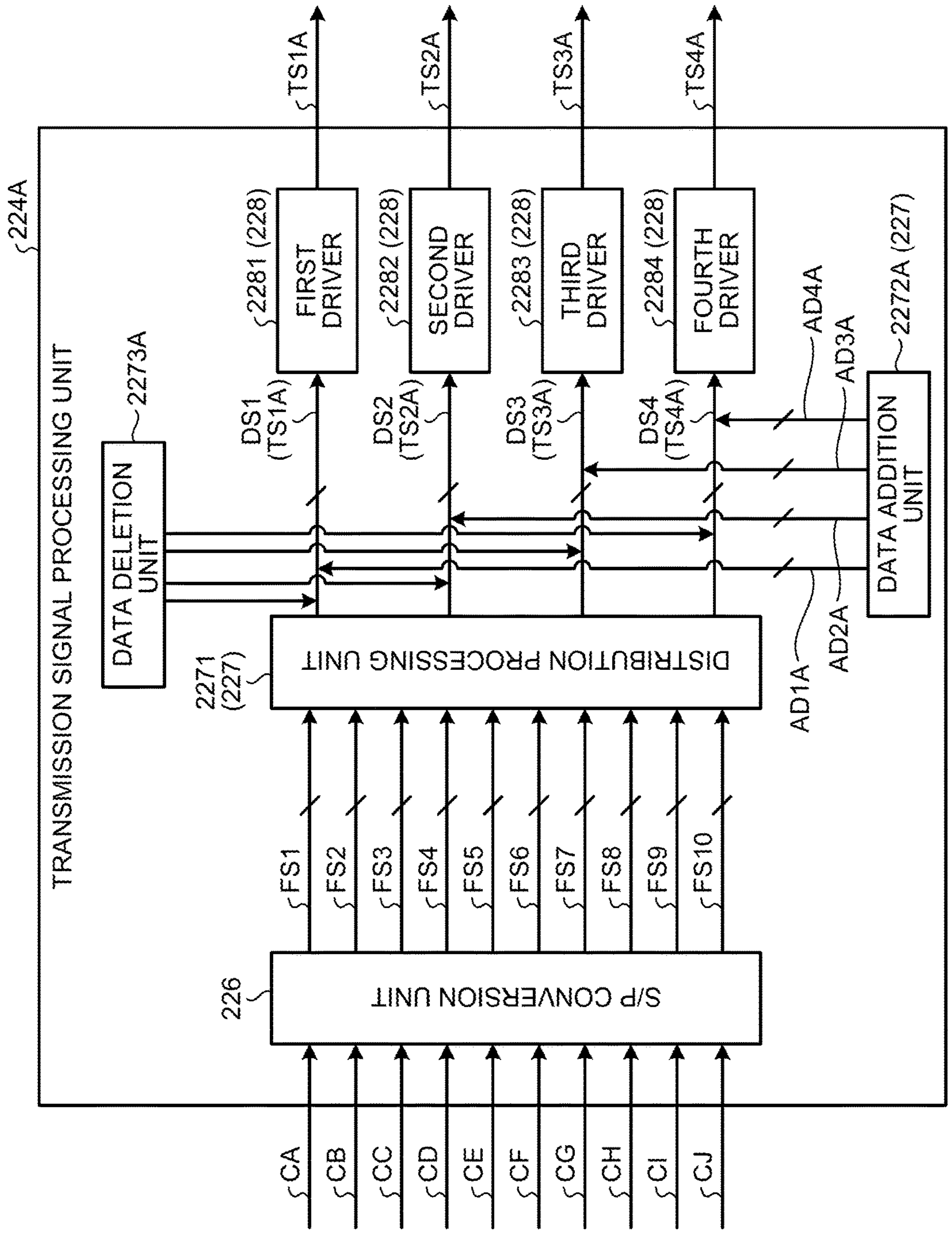
FIG. 14 is a block diagram of the configuration of a transmission signal processing unit illustrated in FIG. 13.
Figure 15:
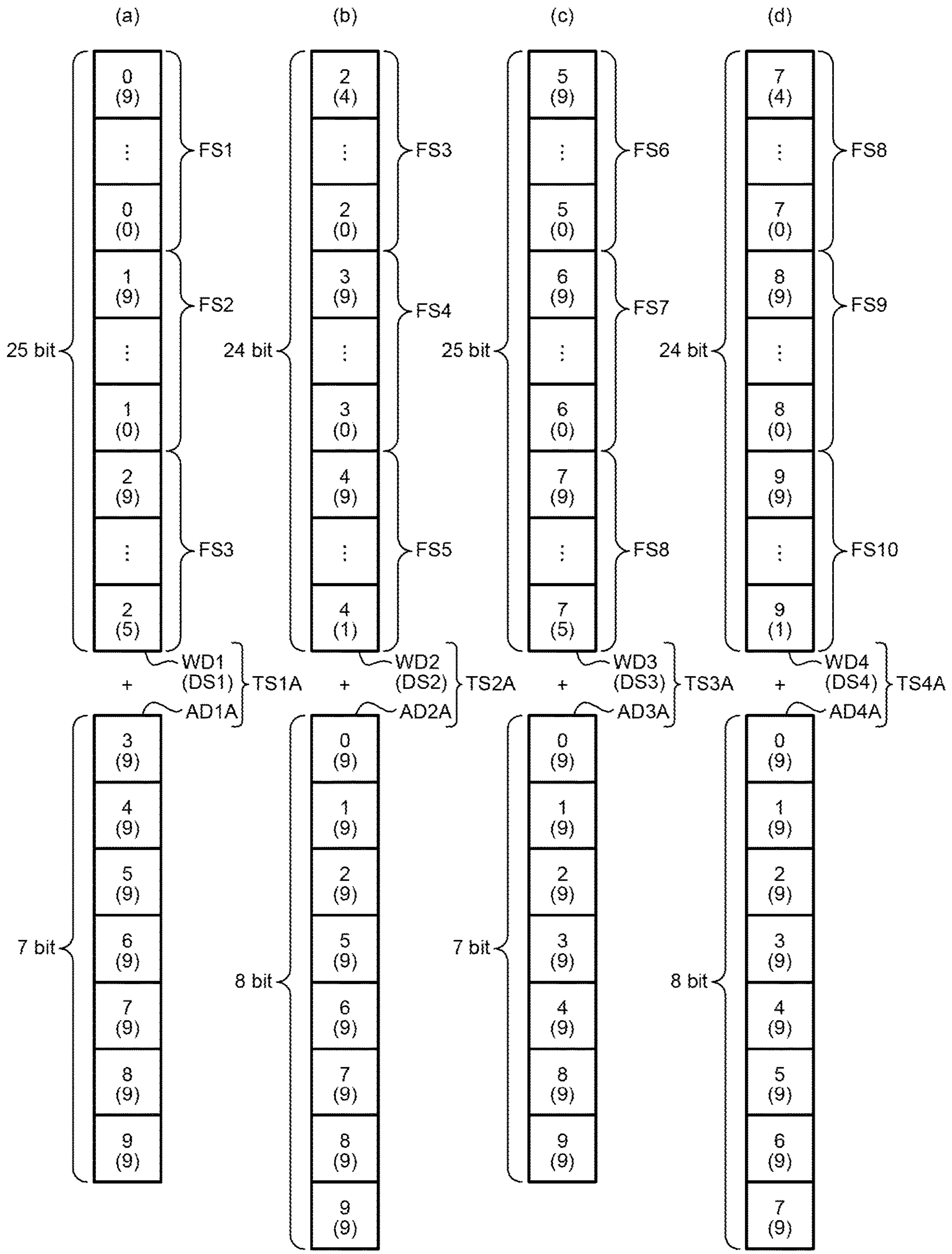
FIG. 15 is a diagram illustrating first to fourth transmission image signals generated at the transmission signal processing unit illustrated in FIGS. 13 and 14.

FIG. 14 is a block diagram of the configuration of the transmission signal processing unit 224A. FIG. 15 is a diagram illustrating first to fourth transmission image signals TS1A to TS4A generated at the transmission signal processing unit 224A. Specifically, FIG. 15 corresponds to FIG. 8 (focusing on the words WD1 to WD4 illustrated in FIG. 6).

As illustrated in FIG. 14, the transmission signal processing unit 224A includes a data deletion unit 2273A in addition to the transmission signal processing unit 224 (FIG. 4) described in the first embodiment above, and a data addition unit 2272A in place of the data addition unit 2272.

The data deletion unit 2273A executes data deletion processing that deletes data of part of at least any of the first to the fourth distributed image signals DS1 to DS4 so that the 8 bits/10 bits conversion processing may be executed at the first to the fourth drivers 2281 to 2284 in accordance with the amount of first to fourth auxiliary data AD1A to AD4A (FIG. 15) added at the data addition unit 2272A.

The following describes the data deletion processing with reference to the words WD1 to WD4 illustrated in FIG. 15.

Specifically, as illustrated in (b) and (d) in FIG. 15, the data deletion unit 2273A deletes data of the LSB of one piece of pixel data (pixel data generated at the pixel of address number “4”) included in the word WD2 (second distributed image signal DS2), and data of the LSB of one piece of pixel data (pixel data generated at the pixel of address number “9”) included in the word WD4 (fourth distributed image signal DS4). Accordingly, the number of bits per word (24 bits) of the second and the fourth distributed image signals DS2 and DS4 part of data of which is deleted at the data deletion unit 2273A is smaller, by one bit, than the number of bits per word (25 bits) of the first and the third distributed image signals DS1 and DS3.

The data addition unit 2272A generates the first to the fourth transmission image signals TS1A to TS1D by adding, as auxiliary data to each of the four of the first to the fourth distributed image signals DS1 to DS4 part of data of which is deleted at the data deletion unit 2273A, data of the MSB of each pixel data included in each of all other distributed image signals.

The following describes the auxiliary data added at the data addition unit 2272A with reference to exemplary auxiliary data added to the words WD1 to WD4 illustrated in FIG. 15.

Specifically, as illustrated in (a) in FIG. 15, the data addition unit 2272A adds, as the first auxiliary data AD1A (7 bits) to the first distributed image signal DS1, data of the MSB of each pixel data (pixel data generated at pixels of address numbers “3” to “9”) included in the second to the fourth distributed image signals DS2 to DS4. As illustrated in (b) in FIG. 15, the data addition unit 2272A adds, as the second auxiliary data AD2A (8 bits) to the second distributed image signal DS2, data of the MSB of each pixel data (pixel data generated at pixels of address numbers “0” to “2” and “5” to “9”) included in the first, third, and fourth distributed image signals DS1, DS3, and DS4. As illustrated in (c) in FIG. 15, the data addition unit 2272A adds, as the third auxiliary data AD3A (7 bits) to the third distributed image signal DS3, data of the MSB of each pixel data (pixel data generated at pixels of address numbers “0” to “4”, “8”, and “9”) included in the first, second, and fourth distributed image signals DS1, DS2, and DS4. As illustrated in (d) in FIG. 15, the data addition unit 2272A adds, as the fourth auxiliary data AD4A (8 bits) to the fourth distributed image signal DS4, data of the MSB of each pixel data (pixel data generated at pixels of address numbers “0” to “7”) included in the first to third distributed image signals DS1 to DS3.

The received signal processing unit 62A has a configuration identical to that of the received signal processing unit 62 described in the first embodiment above, but executes the mapping decoding processing different from that executed by the received signal processing unit 62 when a transmission failure is detected.

Specifically, when a transmission failure is detected, the received signal processing unit 62A (signal restoring unit 623) executes the mapping decoding processing as described below.

For example, when a transmission failure occurs in the first optical fiber 2321 only, the control device 6A is unable to favorably receive the first transmission image signal TS1A through the first optical fiber 2321. In other words, the received signal processing unit 62A is unable to restore the image signals before the mapping processing at the camera head 22A through combination of the first to the fourth distributed image signals DS1 to DS4.

For this reason, the received signal processing unit 62A uses any one of the second to the fourth auxiliary data AD2A to AD4A included in the second to the fourth transmission image signal TS2A to TS4A transmitted through the second to the fourth optical fibers 2322 to 2324. As described above, these second to the fourth auxiliary data AD2A to AD4A include data of the MSB of each pixel data included in the first distributed image signal DS1. Thus, the received signal processing unit 62A restores the first distributed image signal DS1 by using any one of the second to the fourth auxiliary data AD2A to AD4A. Then, the received signal processing unit 62A restores the image signals before the mapping processing at the camera head 22A by combining the this restored first distributed image signal DS1 and the second to the fourth distributed image signals DS2 to DS4 extracted from the second to the fourth transmission image signal TS2A to TS4A after the decoding processing.

The received signal processing unit 62A restores the image signals before the mapping processing at the camera head 22 when a transmission failure occurs in any one of the second to the fourth optical fibers 2322 to 2324 or when transmission failures occur in a plurality (three at maximum) of optical fibers among the first to the fourth optical fibers 2321 to 2324.

Specifically, the first to the fourth distributed image signals DS1 to DS4 each include data of the MSB of each pixel data included in all other distributed image signals, as the corresponding one of the first to the fourth auxiliary data AD1A to AD4A. Thus, when a transmission failure occurs not only in any one of the first to the fourth optical fibers 2321 to 2324 but also in two or three optical fibers thereof, the received signal processing unit 62A restores a distributed image signal corresponding to the optical fiber in which the transmission failure has occurred by using auxiliary data included in a transmission image signal transmitted through an optical fiber in which no transmission failure has occurred.

The medical observation system 1A according to the second embodiment described above achieves an effect described below in addition to the same effect as that of the first embodiment described above.

In the medical observation system 1A according to the second embodiment, the auxiliary data addition processing adds, as auxiliary data to a distributed image signal, data of the MSB of each pixel data included in each of all other distributed image signals different from this distributed image signal.

With this configuration, when transmission failures occur in a plurality (three at maximum) of optical fibers among the first to the fourth optical fibers 2321 to 2324, the control device 6A may restore distributed image signals corresponding to these plurality of optical fibers and appropriately generate display image signals.

In the medical observation system 1A according to the second embodiment, the data deletion processing deletes data of part of the second and the fourth distributed image signals DS2 and DS4.

Through this processing, the amounts of data of the second and the fourth distributed image signals DS2 and DS4 may be adjusted in accordance with the amounts of the second and the fourth auxiliary data AD2A and AD4A so that the 8 bits/10 bits conversion processing may be executed on the second and the fourth transmission image signals TS2A and TS4A.

In particular, in the medical observation system 1A, the data deletion processing deletes data of the LSB of each one piece of pixel data included in the second and the fourth distributed image signals DS2 and DS4.

Important data (more significant digit data) in this one piece of pixel data remains through this processing, thereby reducing influence on the observation image displayed on the display device 4 through the data deletion processing.

Third Embodiment

The following describes a third embodiment of the present disclosure.

In the following description, any component identical to that in the first embodiment described above is denoted by an identical reference sign, and detailed description thereof will be omitted or simplified.

The medical observation system 1 according to the first embodiment described above is not configured to perform feedback (notification) of the transmission failure information from the control device 6 to the camera head 22. In other words, the medical observation system 1 is not configured to execute the auxiliary data addition processing based on the transmission failure information.

However, a medical observation system according to the third embodiment is configured to execute the auxiliary data addition processing based on the transmission failure information.

Figure 16:
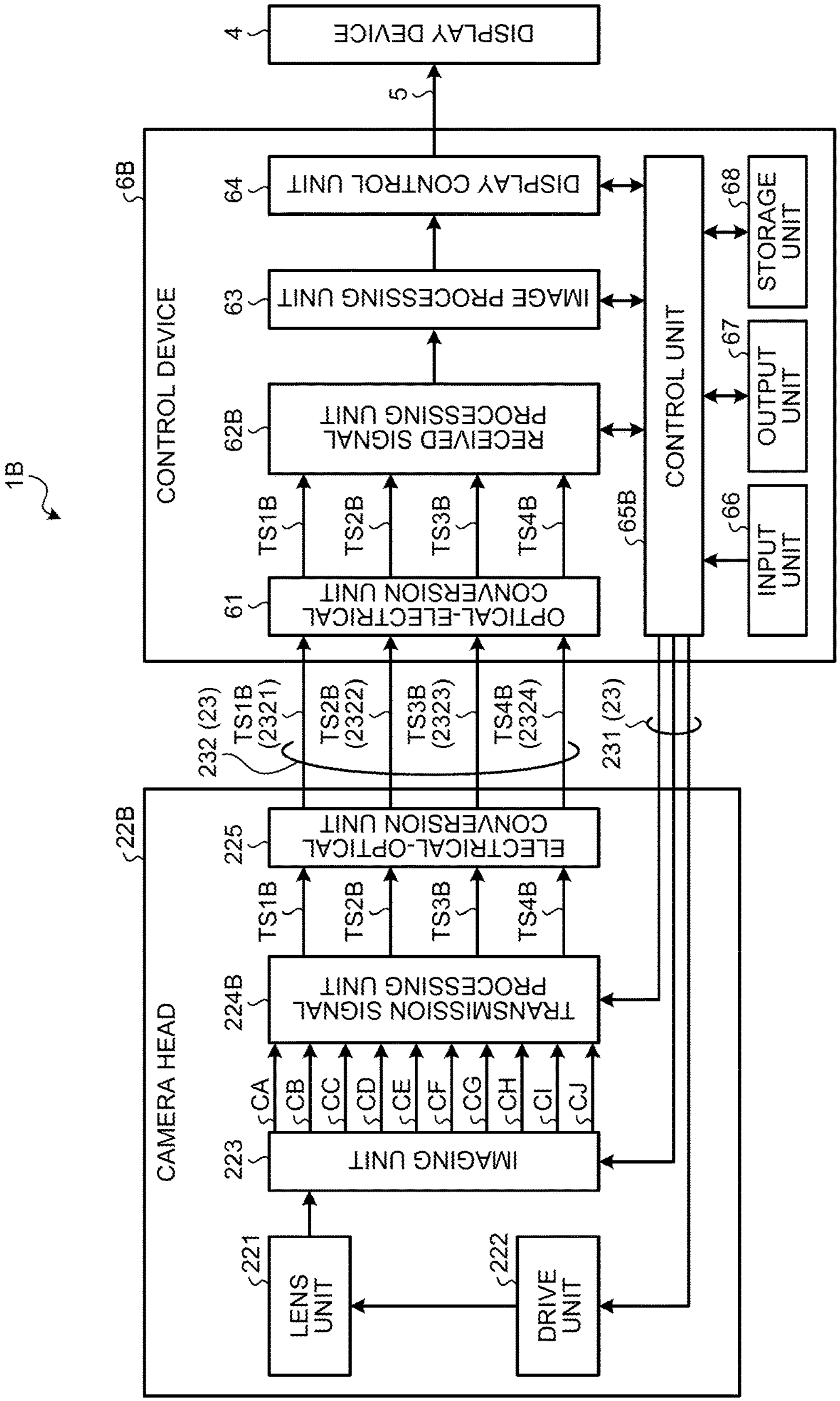
FIG. 16 is a block diagram of the configurations of a camera head and a control device in a medical observation system according to a third embodiment of the present disclosure.

FIG. 16 is a block diagram of the configurations of a camera head 22B and a control device 6B in a medical observation system 1B according to the third embodiment of the present disclosure.

Specifically, unlike the control device 6 (control unit 65) described in the first embodiment above, the control device 6B (a control unit 65B) included in the medical observation system 1B according to the third embodiment is configured to feed back the transmission failure information (information indicating whether a transmission failure has occurred, and, when a transmission failure occurs, an optical fiber in which this transmission failure has occurred) to the camera head 22B (transmission signal processing unit 224B) through the first transmission cable 23 (electric wires 231). The control device 6B includes a received signal processing unit 62B in place of the received signal processing unit 62.

The received signal processing unit 62B has a configuration identical to that of the received signal processing unit 62 described in the first embodiment above, but executes the mapping decoding processing different from that executed by the received signal processing unit 62 when a transmission failure is detected.

This mapping decoding processing will be described in description of the auxiliary data addition processing according to the third embodiment.

As illustrated in FIG. 16, the camera head 22B included in the medical observation system 1B includes a transmission signal processing unit 224B in place of the transmission signal processing unit 224 in the camera head (FIG. 2) described in the first embodiment above.

The transmission signal processing unit 224B has a configuration identical to that of the transmission signal processing unit 224 described in the first embodiment above, but is different from the transmission signal processing unit 224 in that the auxiliary data addition processing is executed based on the transmission failure information (information indicating whether a transmission failure has occurred, and, when a transmission failure occurs, an optical fiber in which this transmission failure has occurred) fed back from the control unit 65B.

Assume that the control device 6B (control unit 65B) provides the camera head 22B (transmission signal processing unit 224B) with feedback to give notification of occurrence of a transmission failure.

In this case, the transmission signal processing unit 224B distributes, into three pieces, each pixel data included in a distributed image signal corresponding to one optical fiber in which a transmission failure has occurred among the four of the first to the fourth distributed image signals DS1 to DS4. Then, the transmission signal processing unit 224B adds these three pieces of distributed data as auxiliary data to three distributed image signals corresponding to three optical fibers in which no transmission failure has occurred.

The following describes the auxiliary data added at the transmission signal processing unit 224B with reference to auxiliary data added to the words WD1 to WD4 illustrated in FIGS. 6 and 7. The description is sequentially made on a case in which a transmission failure occurs in the first optical fiber 2321, a case in which a transmission failure occurs in the second optical fiber 2322, a case in which a transmission failure occurs in the third optical fiber 2323, and a case in which a transmission failure occurs in the fourth optical fiber 2324.

Figure 17:
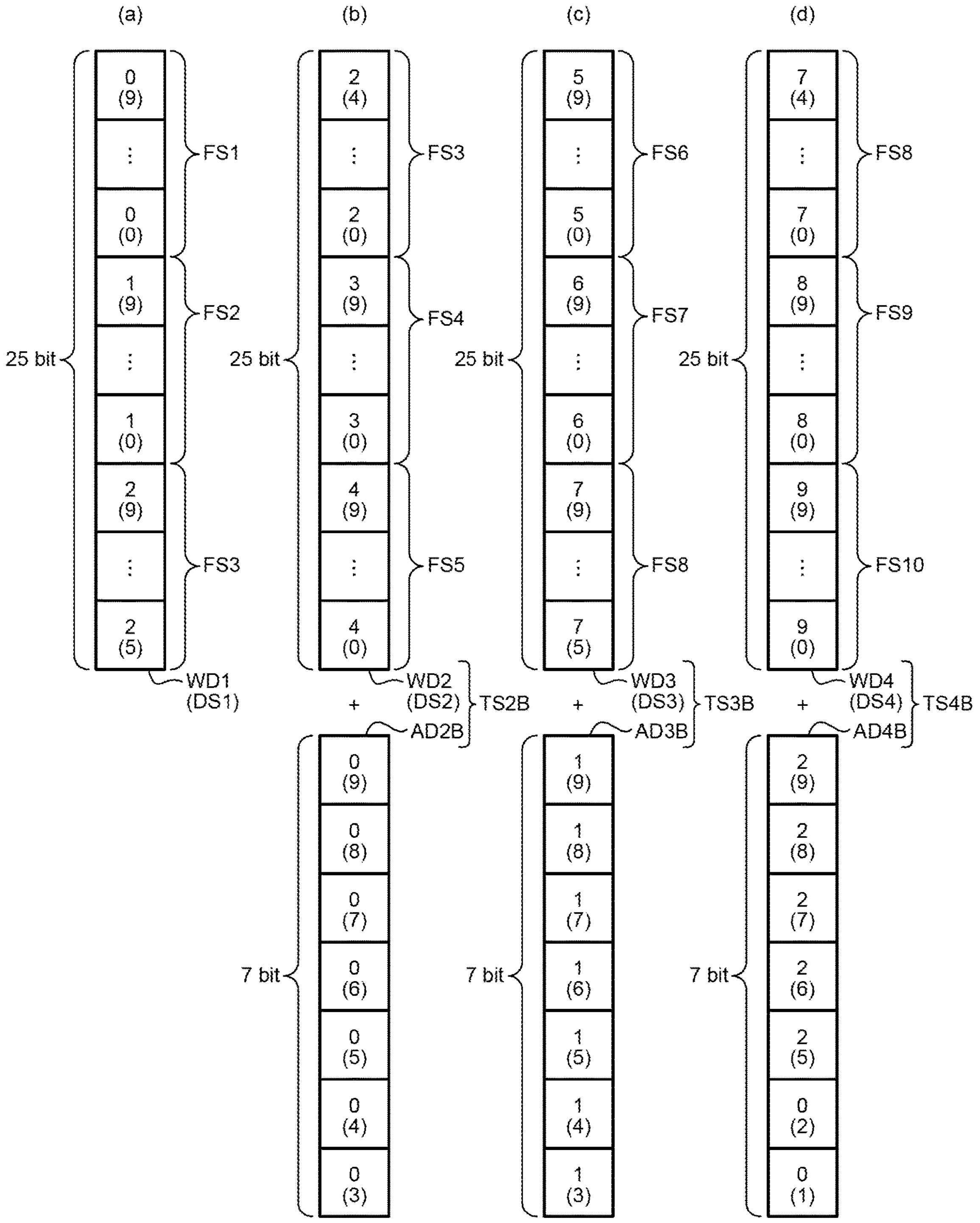
FIG. 17 is a diagram illustrating second to fourth auxiliary data added at a transmission signal processing unit when a transmission failure occurs in a first optical fiber illustrated in FIG. 16.

FIG. 17 is a diagram illustrating second to fourth auxiliary data AD2B to AD4B added at the transmission signal processing unit 224B when a transmission failure occurs in the first optical fiber 2321. Specifically, FIG. 17 corresponds to FIG. 8 (focusing on the words WD1 to WD4 illustrated in FIG. 6).

When a transmission failure occurs in the first optical fiber 2321, the transmission signal processing unit 224B distributes, into three pieces, each pixel data included in the first distributed image signal DS1. Specifically, as illustrated in FIG. 17, the transmission signal processing unit 224B distributes the word WD1 (first distributed image signal DS1) into data (the second auxiliary data AD2B (7 bits)) at bit positions "9" to "3" in pixel data generated at the pixel of address number "0", data (the third auxiliary data AD3B (7 bits)) at bit positions "9" to "3" in pixel data generated at the pixel of address number "1", data (5 bits) at bit positions "9" to "5" in pixel data generated at the pixel of address number "2", and other 2-bit data (the fourth auxiliary data AD4B (7 bits)). In the third embodiment, as illustrated in (d) in FIG. 17, the other 2-bit data described above is data at bit positions "2" and "1" in pixel data generated at the pixel of address number "0", but the present disclosure is not limited thereto. The other 2-bit data may be any other data. Then, the transmission signal processing unit 224B generates a second transmission image signal TS2B ((b) in FIG. 17) by adding the second auxiliary data AD2B to the second distributed image signal DS2, generates a third transmission image signal TS3B ((c) in FIG. 17) by adding the third auxiliary data AD3B to the third distributed image signal DS3, and generates a fourth transmission image signal TS4B ((d) in FIG. 17) by adding the fourth auxiliary data AD4B to the fourth distributed image signal DS4.

Then, the received signal processing unit 62B executes the mapping decoding processing described below.

Specifically, the received signal processing unit 62B restores the first distributed image signal DS1 by using the second to the fourth auxiliary data AD2B to AD4B included in the second to the fourth transmission image signals TS2B to TS4B transmitted through the second to the fourth optical fibers 2322 to 2324. Then, the received signal processing unit 62B restores the image signals before the mapping processing at the camera head 22B by combining the restored first distributed image signal DS1 and the second to the fourth distributed image signals DS2 to DS4 extracted from the second to the fourth transmission image signals TS2B to TS4B.

Figure 18:
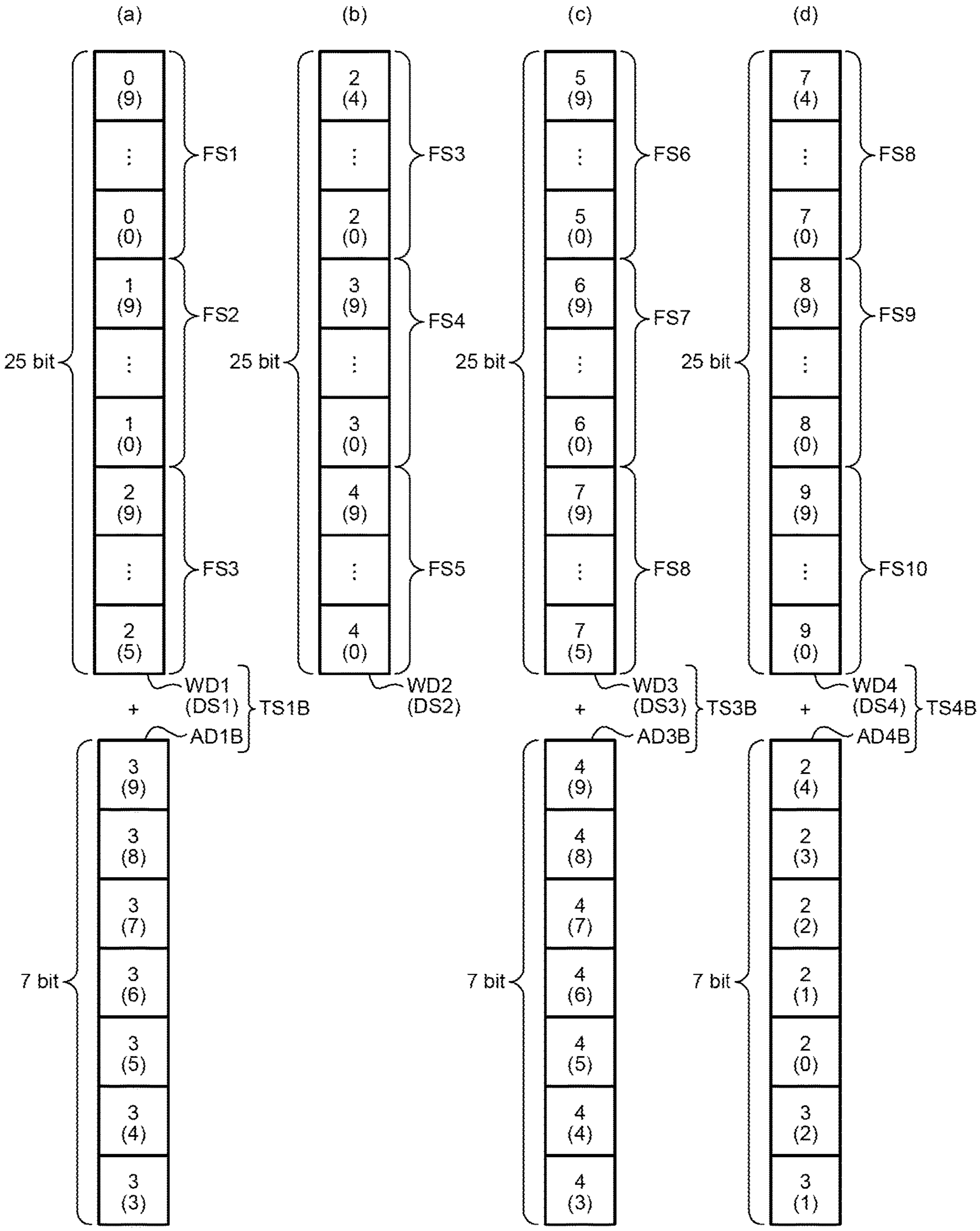
FIG. 18 is a diagram illustrating first, third, and fourth auxiliary data added at the transmission signal processing unit when a transmission failure occurs in a second optical fiber illustrated in FIG. 16.

FIG. 18 is a diagram illustrating the first, third, and fourth auxiliary data AD1B, AD3B, and AD4B added at the transmission signal processing unit 224B when a transmission failure occurs in the second optical fiber 2322. Specifically, FIG. 18 corresponds to FIG. 8 (focusing on the words WD1 to WD4 illustrated in FIG. 6).

When a transmission failure occurs in the second optical fiber 2322, the transmission signal processing unit 224B distributes, into three pieces, each pixel data included in the second distributed image signal DS2. Specifically, as illustrated in FIG. 18, the transmission signal processing unit 224B distributes the word WD2 (second distributed image signal DS2) into data (the first auxiliary data AD1B (7 bits)) at bit positions "9" to "3" in pixel data generated at the pixel of address number "3", data (the third auxiliary data AD3B (7 bits)) at bit positions "9" to "3" in pixel data generated at the pixel of address number "4", data (5 bits) at bit positions "4" to "0" in pixel data generated at the pixel of address number "2", and other 2-bit data (the fourth auxiliary data AD4B (7 bits)). In the third embodiment, as illustrated in (d) in FIG. 18, the other 2-bit data described above is data at bit positions "2" and "1" in pixel data generated at the pixel of address number "3", but the present disclosure is not limited thereto. The other 2-bit data may be any other data. Then, the transmission signal processing unit 224B generates a first transmission image signal TS1B ((a) in FIG. 18) by adding the first auxiliary data AD1B to the first distributed image signal DS1, generates the third transmission image signal TS3B ((c) in FIG. 18) by adding the third auxiliary data AD3B to the third distributed image signal DS3, and generates the fourth transmission image signal TS4B ((d) in FIG. 18) by adding the fourth auxiliary data AD4B to the fourth distributed image signal DS4.

Then, the received signal processing unit 62B executes the mapping decoding processing described below.

Specifically, the received signal processing unit 62B restores the second distributed image signal DS2 by using the first, third, and fourth auxiliary data AD1B, AD3B, and AD4B included in the first, third, and fourth transmission image signals TS1B, TS3B, and TS4B transmitted through the first, third, and fourth optical fibers 2321, 2323, and 2324. Then, the received signal processing unit 62B restores the image signals before the mapping processing at the camera head 22B by combining the restored second distributed image signal DS2, and the first, third, and fourth distributed image signals DS1, DS3, and DS4 extracted from the first, third, and fourth transmission image signals TS1B, TS3B, and TS4B.

Figure 19:
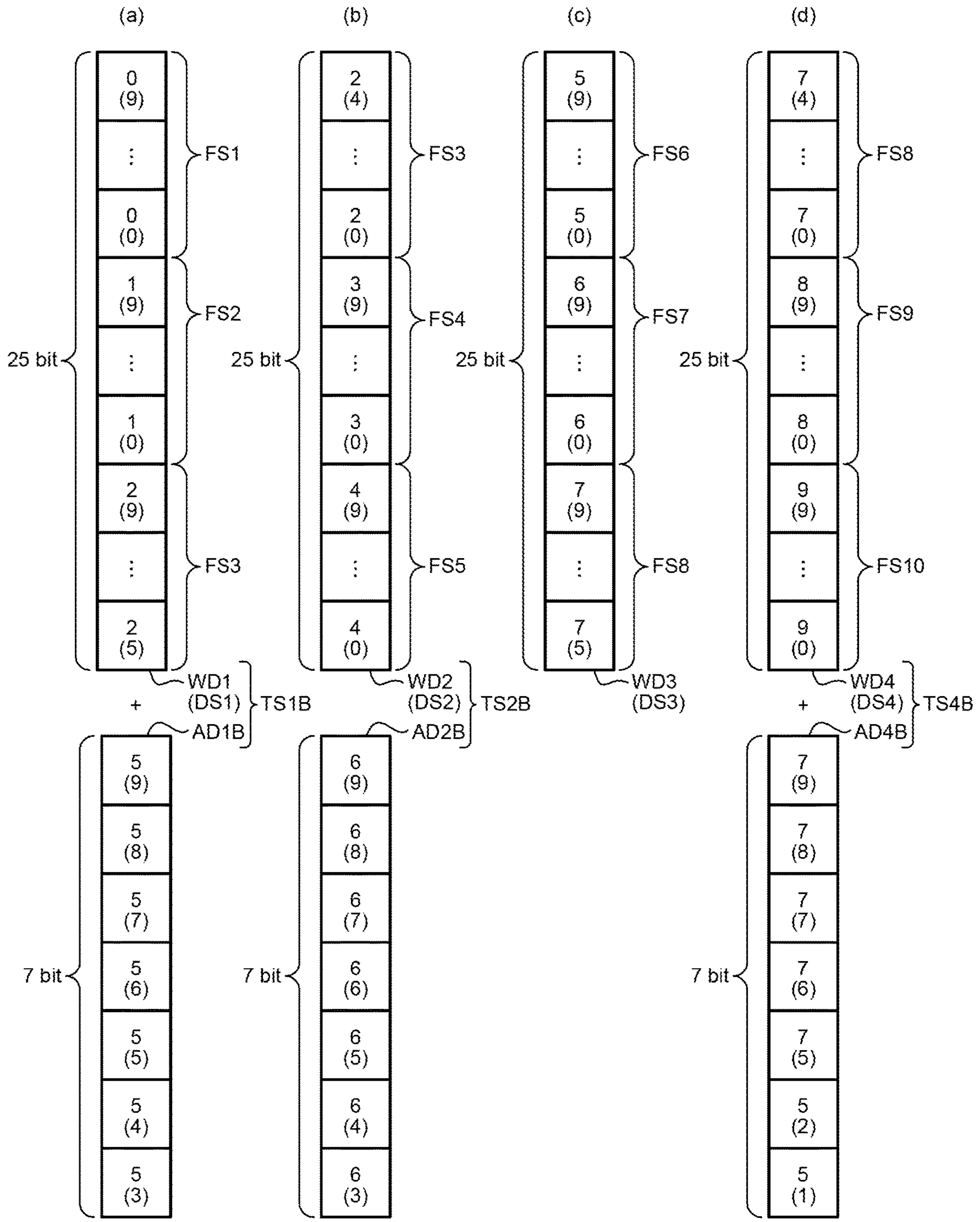
FIG. 19 is a diagram illustrating first, second, and fourth auxiliary data added at the transmission signal processing unit when a transmission failure occurs in a third optical fiber illustrated in FIG. 16.

FIG. 19 is a diagram illustrating the first, second, and fourth auxiliary data AD1B, AD2B, and AD4B added at the transmission signal processing unit 224B when a transmission failure occurs in the third optical fiber 2323. Specifically, FIG. 19 corresponds to FIG. 8 (focusing on the words WD1 to WD4 illustrated in FIG. 6).

When a transmission failure occurs in the third optical fiber 2323, the transmission signal processing unit 224B distributes, into three pieces, each pixel data included in the third distributed image signal DS3. Specifically, as illustrated in FIG. 19, the transmission signal processing unit 224B distributes the word WD3 (third distributed image signal DS3) into data (the first auxiliary data AD1B (7 bits)) at bit positions "9" to "3" in pixel data generated at the pixel of address number "5", data (the second auxiliary data AD2B (7 bits)) at bit positions "9" to "3" in pixel data generated at the pixel of address number "6", data (4 bits) at bit positions "9" to "5" in pixel data generated at the pixel of address number "7", and other 2-bit data (the fourth auxiliary data AD4B (7 bits)). In the third embodiment, as illustrated in (d) in FIG. 19, the other 2-bit data described above is data at bit positions "2" and "1" in pixel data generated at the pixel of address number "5", but the present disclosure is not limited thereto. The other 2-bit data may be any other data. Then, the transmission signal processing unit 224B generates the first transmission image signal TS1B ((a) in FIG. 19) by adding the first auxiliary data AD1B to the first distributed image signal DS1, generates the second transmission image signal TS2B ((b) in FIG. 19) by adding the second auxiliary data AD2B to the second distributed image signal DS2, and generates the fourth transmission image signal TS4B ((d) in FIG. 19) by adding the fourth auxiliary data AD4B to the fourth distributed image signal DS4.

Then, the received signal processing unit 62B executes the mapping decoding processing described below.

Specifically, the received signal processing unit 62B restores the third distributed image signal DS3 by using the first, second, and fourth auxiliary data AD1B, AD2B, and AD4B included in the first, second, and fourth transmission image signal TS1B, TS2B, and TS4B transmitted through the first, second, and fourth optical fibers 2321, 2322, and 2324. Then, the received signal processing unit 62B restores the image signals before the mapping processing at the camera head 22B by combining the restored third distributed image signal DS3, and the first, second, and fourth distributed image signals DS1, DS2, and DS4 extracted from the first, second, and fourth transmission image signal TS1B, TS2B, and TS4B.

Figure 20:
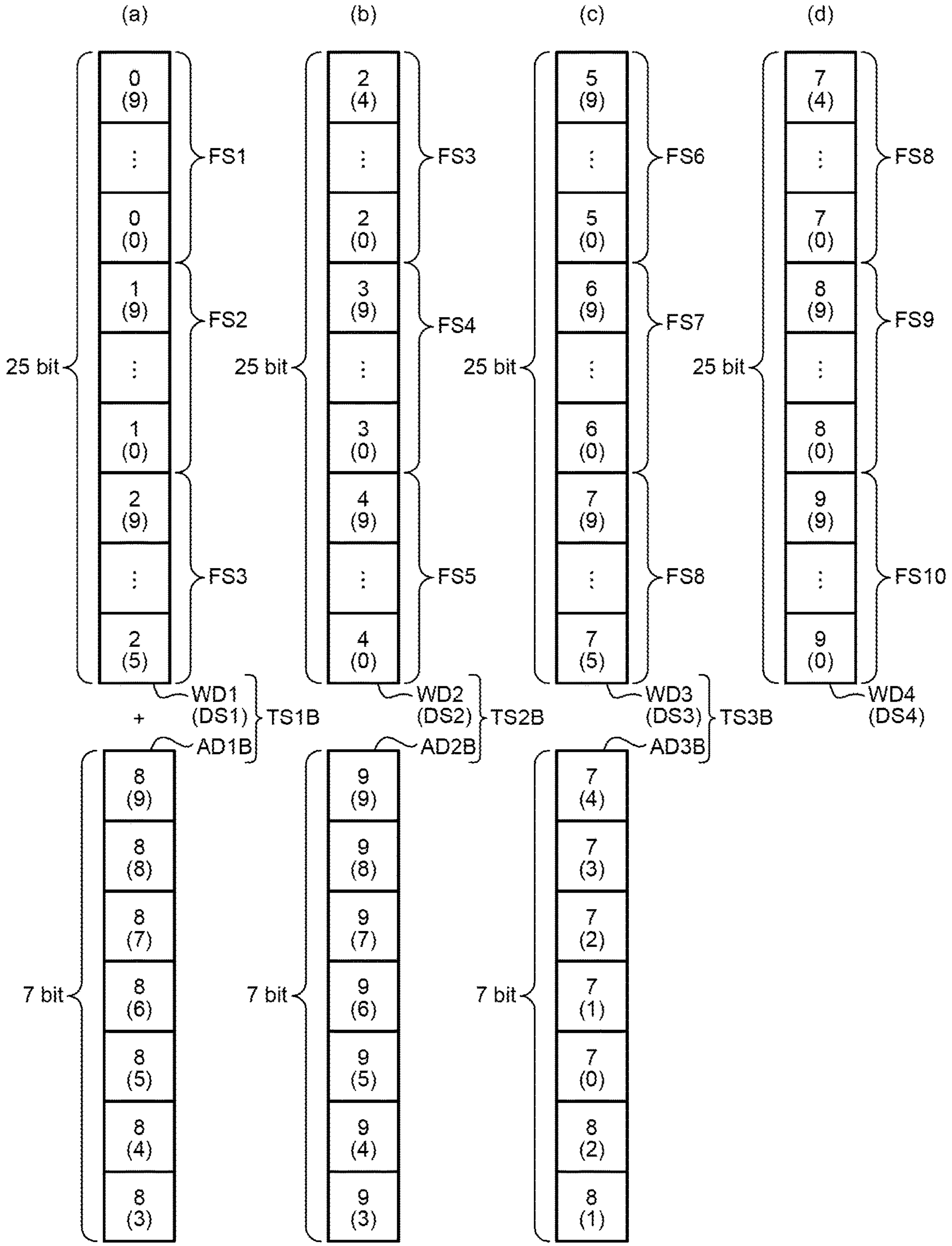
FIG. 20 is a diagram illustrating first to third auxiliary data added at the transmission signal processing unit when a transmission failure occurs in a fourth optical fiber illustrated in FIG. 16.

FIG. 20 is a diagram illustrating the first to third auxiliary data AD1B to AD3B added at the transmission signal processing unit 224B when a transmission failure occurs in the fourth optical fiber 2324. Specifically, FIG. 20 corresponds to FIG. 8 (focusing on the words WD1 to WD4 illustrated in FIG. 6).

When a transmission failure occurs in the fourth optical fiber 2324, the transmission signal processing unit 224B distributes, into three pieces, each pixel data included in the fourth distributed image signal DS4. Specifically, as illustrated in FIG. 20, the transmission signal processing unit 224B distributes the word WD4 (fourth distributed image signal DS4) into data (the first auxiliary data AD1B (7 bits)) at bit positions "9" to "3" in pixel data generated at the pixel of address number "8", data (the second auxiliary data AD2B (7 bits)) at bit positions "9" to "3" in pixel data generated at the pixel of address number "9", data (5 bits) at bit positions "4" to "0" in pixel data generated at the pixel of address number "7", and other 2-bit data (the third auxiliary data AD3B (7 bits)). In the third embodiment, as illustrated in (c) in FIG. 20, the other 2-bit data described above is data at bit positions "2" and "1" in pixel data generated at the pixel of address number "8", but the present disclosure is not limited thereto. The other 2-bit data may be any other data. Then, the transmission signal processing unit 224B generates the first transmission image signal TS1B ((a) in FIG. 20) by adding the first auxiliary data AD1B to the first distributed image signal DS1, generates the second transmission image signal TS2B ((b) in FIG. 20) by adding the second auxiliary data AD2B to the second distributed image signal DS2, and generates the third transmission image signal TS3B ((c) in FIG. 20) by adding the third auxiliary data AD3B to the third distributed image signal DS3.

Then, the received signal processing unit 62B executes the mapping decoding processing described below.

Specifically, the received signal processing unit 62B restores the fourth distributed image signal DS4 by using the first to third auxiliary data AD1B to AD3B included in the first to third transmission image signals TS1B to TS3B transmitted through the first to third optical fibers 2321 to 2323. Then, the received signal processing unit 62B restores the image signals before the mapping processing at the camera head 22B by combining the restored fourth distributed image signal DS4, and the first to third distributed image signals DS1 to DS3 extracted from the first to third transmission image signals TS1B to TS3B.

Next, assume that the control device 6B (control unit 65B) provides the camera head 22B (transmission signal processing unit 224B) with feedback to give notification of no occurrence of a transmission failure.

In this case, the control device 6B does not perform restoring of the first to the fourth distributed image signals DS1 to DS4 in the mapping decoding processing. In other words, the first to the fourth auxiliary data AD1B to AD4B described above is not used in the mapping decoding processing. Thus, the first to the fourth auxiliary data added to the first to the fourth distributed image signals DS1 to DS4 through the auxiliary data addition processing may be any data that allows execution of the 8 bits/10 bits conversion processing at a later stage.

The medical observation system 1B according to the third embodiment described above achieves an effect described below in addition to the same effect as that of the first embodiment described above.

In the medical observation system 1B according to the third embodiment, the auxiliary data addition processing is executed based on the transmission failure information.

Thus, no auxiliary data needs be added to a distributed image signal corresponding to an optical fiber in which a transmission failure has occurred, thereby reducing a processing load on the transmission signal processing unit 224B.

Fourth Embodiment

The following describes a fourth embodiment of the present disclosure.

In the following description, any configuration identical to those in the first and the third embodiments described above is denoted by an identical reference sign, and detailed description thereof will be omitted or simplified.

The medical observation system 1B according to the third embodiment described above is configured to deal with a case in which a transmission failure occurs in one of the first to the fourth optical fibers 2321 to 2324.

However, a medical observation system according to the fourth embodiment is configured to deal with a case in which transmission failures occur in a plurality (three at maximum) of optical fibers among the first to the fourth optical fibers 2321 to 2324, and is configured to execute the transmission signal generation processing (the mapping processing and the auxiliary data addition processing) and the mapping decoding processing different from those executed by the medical observation system 1B described in the third embodiment above.

Figure 21:
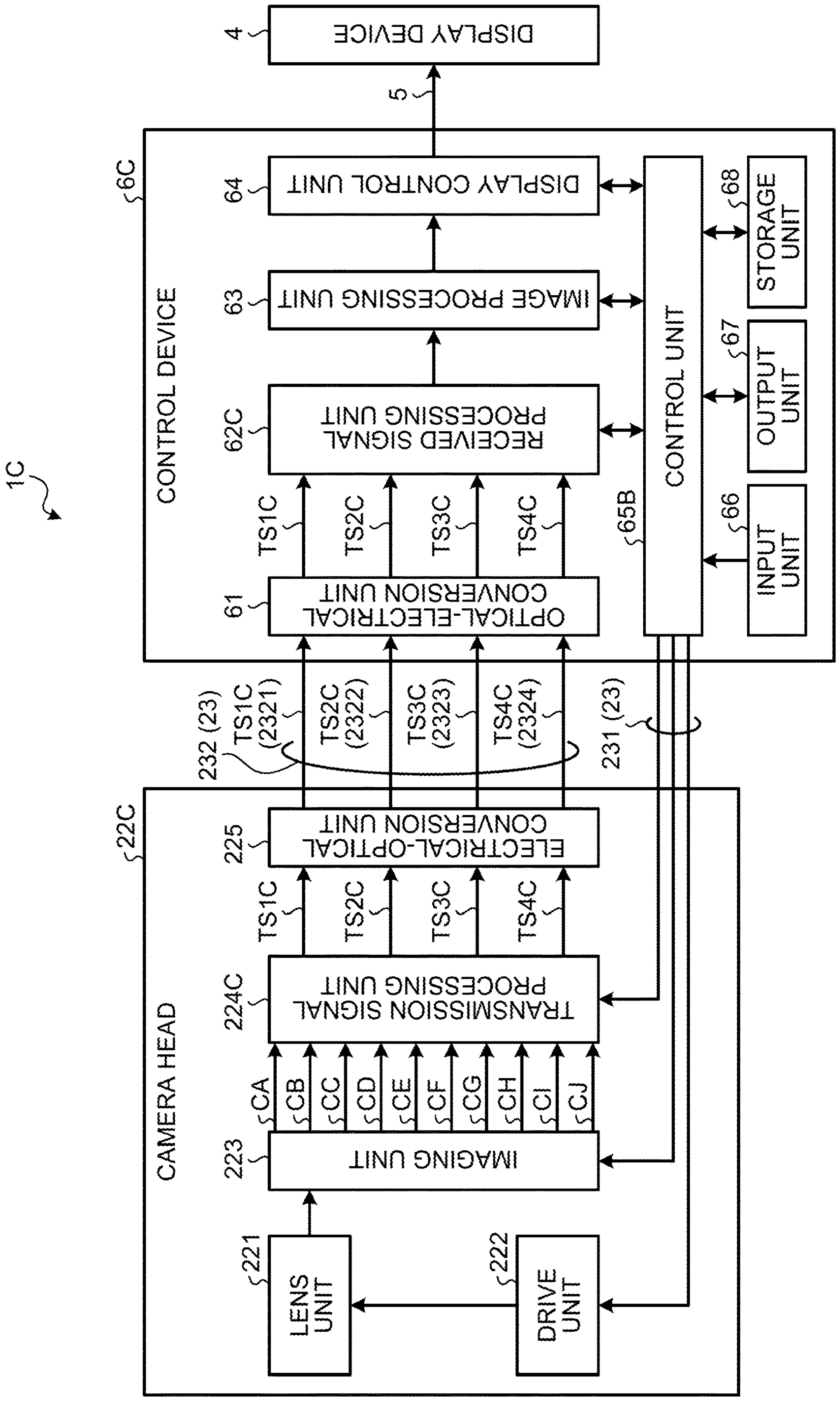
FIG. 21 is a block diagram of the configurations of a camera head and a control device in a medical observation system according to a fourth embodiment of the present disclosure.

FIG. 21 is a block diagram of the configurations of a camera head 22C and a control device 6C in a medical observation system 1C according to the fourth embodiment of the present disclosure.

Specifically, as illustrated in FIG. 21, the medical observation system 1C according to the fourth embodiment includes a transmission signal processing unit 224C and a received signal processing unit 62C in place of the transmission signal processing unit 224B and the received signal processing unit 62B in the medical observation system 1B (FIG. 16) described in the third embodiment above.

The received signal processing unit 62C has a configuration identical to that of the received signal processing unit 62B described in the third embodiment above, but executes the mapping decoding processing different from that executed by the received signal processing unit 62B when a transmission failure is detected.

This mapping decoding processing will be described in description of the auxiliary data addition processing by the transmission signal processing unit 224C.

Figure 22:
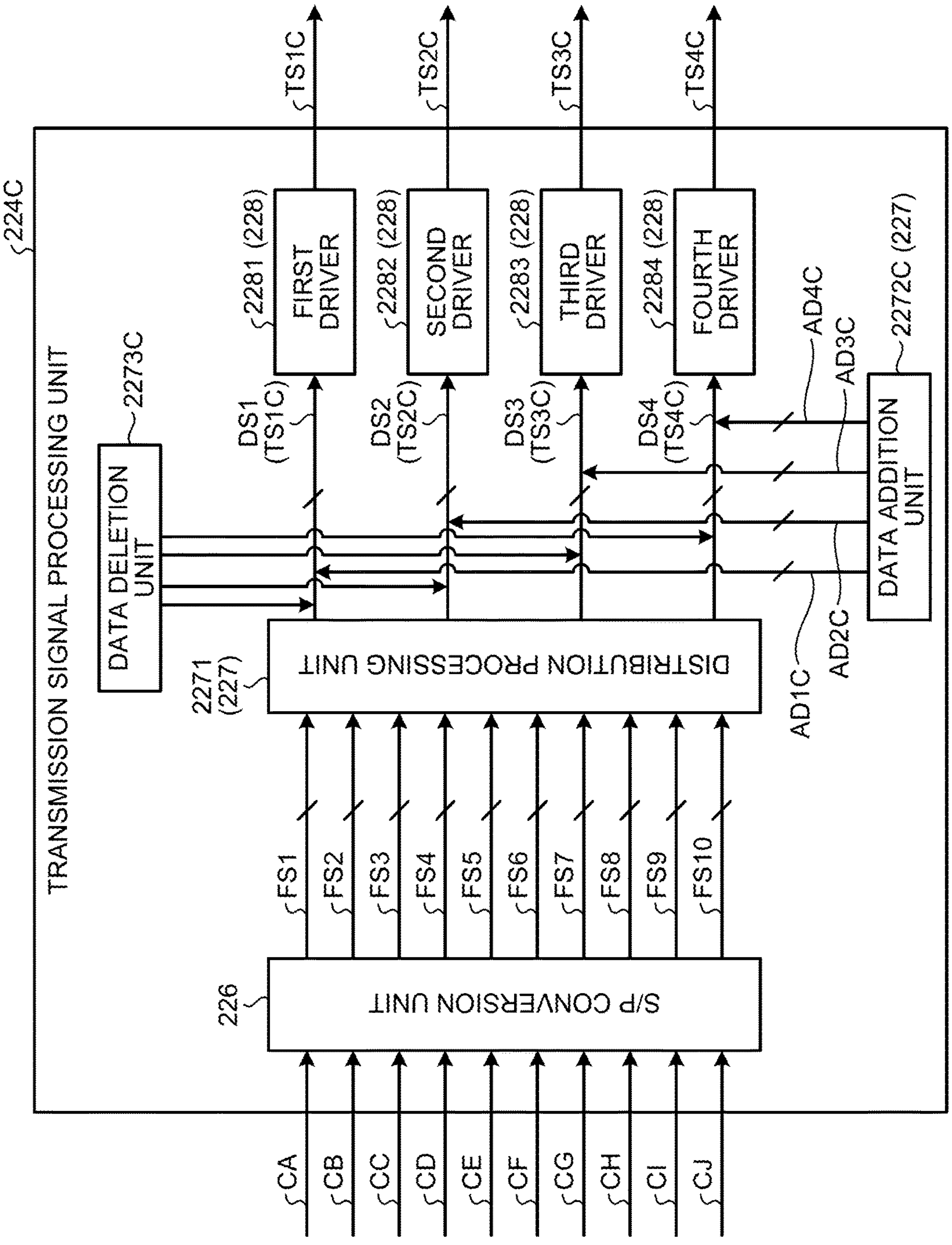
FIG. 22 is a block diagram of the configuration of a transmission signal processing unit illustrated in FIG. 21.

FIG. 22 is a block diagram of the configuration of the transmission signal processing unit 224C.

The transmission signal processing unit 224C includes a data deletion unit 2273C in addition to the transmission signal processing unit 224 (FIG. 4) described in the first embodiment above, and a data addition unit 2272C in place of the data addition unit 2272.

The data deletion unit 2273C executes the data deletion processing that deletes data of part of at least any of the first to the fourth distributed image signals DS1 to DS4 in accordance with the amount of the first to the fourth auxiliary data added at the data addition unit 2272A so that the 8 bits/10 bits conversion processing may be executed at the first to the fourth drivers 2281 to 2284.

This data deletion processing will be described in description of the auxiliary data addition processing by the data addition unit 2272C.

The data addition unit 2272C is different from the data addition unit 2272 described in the first embodiment above in that the auxiliary data addition processing is executed based on the transmission failure information (information indicating whether a transmission failure has occurred, and, when a transmission failure occurs, an optical fiber in which this transmission failure has occurred) fed back from the control unit 65B.

Assume that the control device 6C (control unit 65B) provides the camera head 22C (transmission signal processing unit 224C) with feedback to give notification of occurrence of a transmission failure.

In this case, the data addition unit 2272C adds, as auxiliary data to a distributed image signal corresponding to one optical fiber in which no transmission failure has occurred among the four of the first to the fourth distributed image signals DS1 to DS4, data of the MSB of each pixel data included in distributed image signals corresponding to the other three optical fibers. When no transmission failure occurs in any of the other three optical fibers, the data addition unit 2272C adds appropriate data as auxiliary data to a distributed image signal corresponding to this optical fiber so that the 8 bits/10 bits conversion processing may be executed at a later stage.

The following describes the auxiliary data added at the data addition unit 2272C with reference to auxiliary data added to the words WD1 to WD4 illustrated in FIGS. 6 and 7. The description is sequentially made on a case in which no transmission failure occurs in the first optical fiber 2321, a case in which no transmission failure occurs in the second optical fiber 2322, a case in which no transmission failure occurs in the third optical fiber 2323, and a case in which no transmission failure occurs in the fourth optical fiber 2324.

Figure 23:
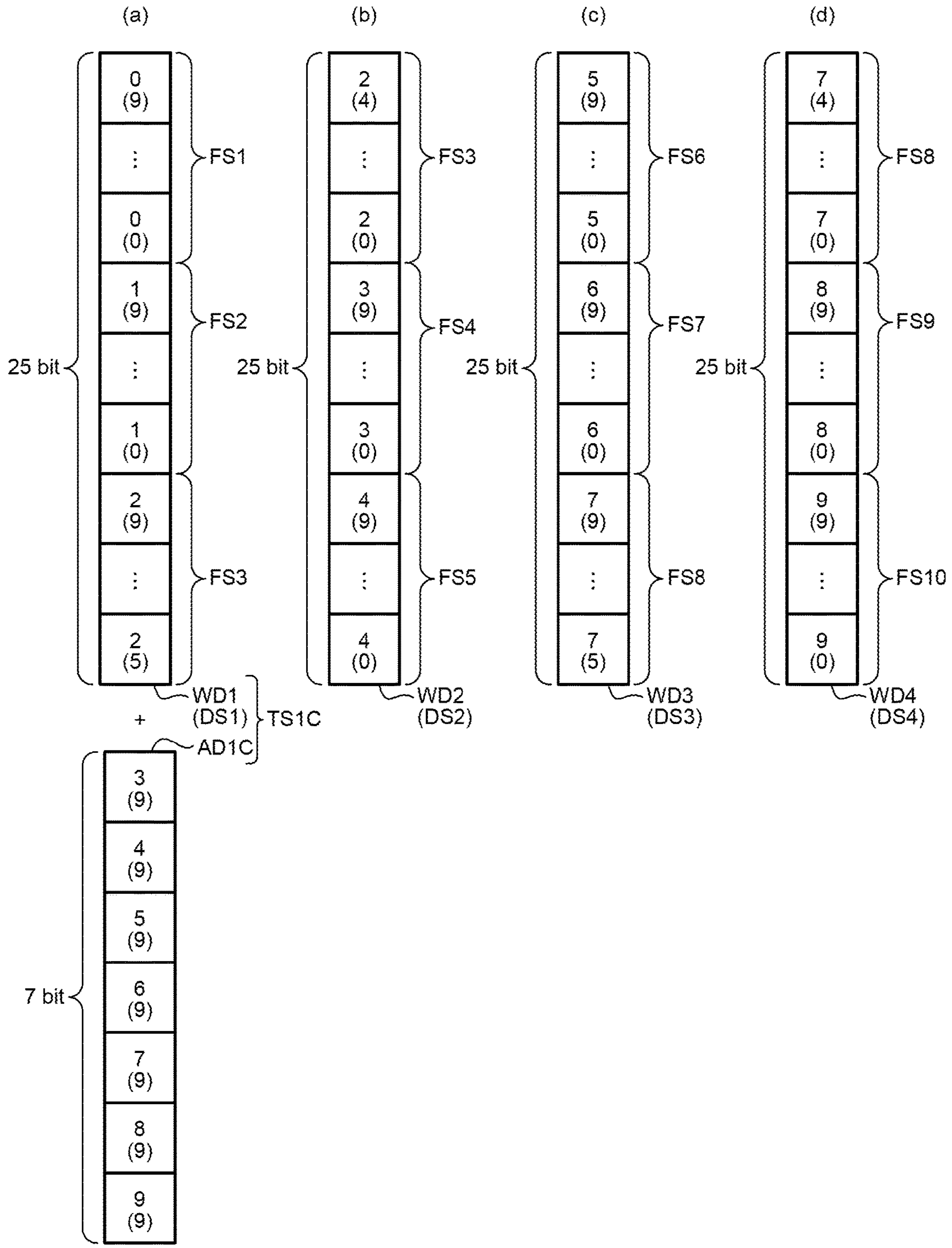
FIG. 23 is a diagram illustrating first auxiliary data added at a data addition unit when no transmission failure occurs in a first optical fiber illustrated in FIG. 21.

FIG. 23 is a diagram illustrating first auxiliary data AD1C added at the data addition unit 2272C when no transmission failure occurs in the first optical fiber 2321. Specifically, FIG. 23 corresponds to FIG. 8 (focusing on the words WD1 to WD4 illustrated in FIG. 6). For the purpose of description, FIG. 23 illustrates an example in which transmission failures have occurred in the three optical fibers of the second to the fourth optical fibers 2322 to 2324.

When no transmission failure occurs in the first optical fiber 2321 (when a transmission failure occurs in at least any of the second to the fourth optical fibers 2322 to 2324), the data addition unit 2272C uses, as the first auxiliary data AD1C of the first distributed image signal DS1, data (7 bits) of the MSB of each pixel data included in the second to the fourth distributed image signals DS2 to DS4. Specifically, as illustrated in (a) in FIG. 23, the first auxiliary data AD1C includes data of the MSB of each pixel data generated pixels of address numbers “3” and “4” included in the word WD2 (second distributed image signal DS2), data of the MSB of pixel data generated at pixels of address numbers “5” to “7” included in the word WD3 (third distributed image signal DS3), and data of the MSB of each of pieces of pixel data generated at pixels of address numbers “8” and “9” included in the word WD4 (fourth distributed image signal DS4). Then, the data addition unit 2272C generates a first transmission image signal TS1C ((a) in FIG. 23) by adding the first auxiliary data AD1C to the first distributed image signal DS1.

Then, the received signal processing unit 62C executes the mapping decoding processing described below.

Specifically, the received signal processing unit 62C restores a distributed image signal corresponding to an optical fiber in which a transmission failure has occurred by using the first auxiliary data AD1C included in the first transmission image signal TS1C transmitted through the first optical fiber 2321. For example, when a transmission failure occurs in the second optical fiber 2322, the received signal processing unit 62C restores the second distributed image signal DS2 by using data of the MSB of each of pieces of pixel data generated at pixels of address numbers “3” and “4” included in the first auxiliary data AD1C. When a transmission failure occurs in the third optical fiber 2323, the received signal processing unit 62C restores the third distributed image signal DS3 by using data of the MSB of pixel data generated at pixels of address numbers “5” to “7” included in the first auxiliary data AD1C. When a transmission failure occurs in the fourth optical fiber 2324, the received signal processing unit 62C restores the fourth distributed image signal DS4 by using data of the MSB of each of pieces of pixel data generated at pixels of address numbers “8” and “9” included in the first auxiliary data AD1C. Then, the received signal processing unit 62C restores the image signals before the mapping processing at the camera head 22C by combining this restored distributed image signal and a distributed image signal extracted from a transmission image signal transmitted through an optical fiber in which no transmission failure has occurred.

When no transmission failure occurs in any of the second to the fourth optical fibers 2322 to 2324 other than the first optical fiber 2321, the received signal processing unit 62C does not use auxiliary data included in a transmission image signal transmitted through this optical fiber in the mapping decoding processing. Thus, auxiliary data added to a distributed image signal corresponding to this optical fiber in the auxiliary data addition processing may be any data that allows execution of the 8 bits/10 bits conversion processing at a later stage.

Figure 24:
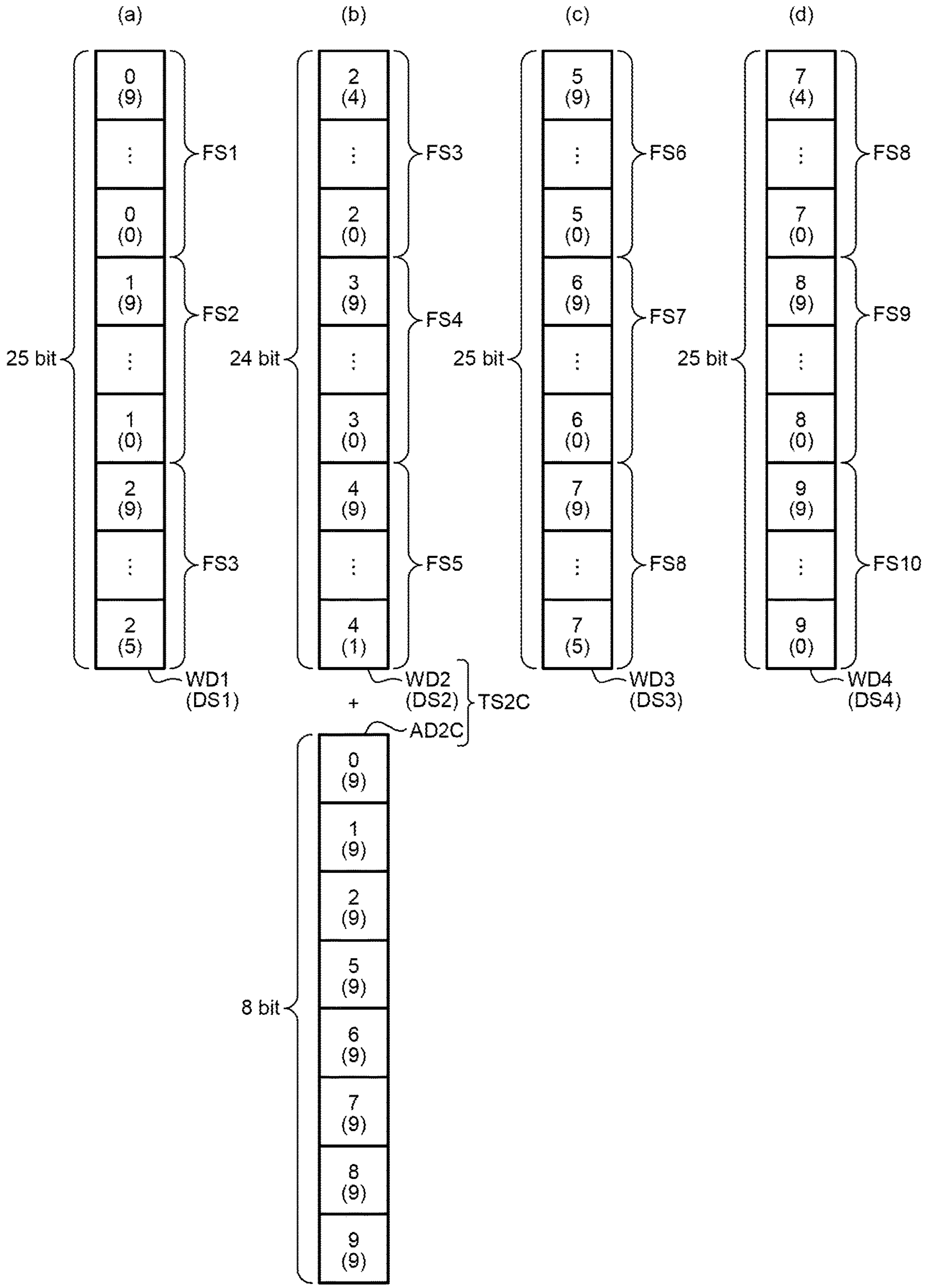
FIG. 24 is a diagram illustrating second auxiliary data added at the data addition unit when no transmission failure occurs in a second optical fiber illustrated in FIG. 21.

FIG. 24 is a diagram illustrating second auxiliary data AD2C added at the data addition unit 2272C when no transmission failure occurs in the second optical fiber 2322. Specifically, FIG. 24 corresponds to FIG. 8 (focusing on the words WD1 to WD4 illustrated in FIG. 6). For the purpose of description, FIG. 24 illustrates an example in which transmission failures have occurred in the three optical fibers of the first, third, and fourth optical fibers 2321, 2323, and 2324.

When no transmission failure occurs in the second optical fiber 2322 (when a transmission failure occurs in at least any of the first, third, and fourth optical fibers 2321, 2323, and 2324), the data addition unit 2272C uses, as the second auxiliary data AD2C of the second distributed image signal DS2, data (8 bits) of the MSB of each pixel data included in the first, third, and fourth distributed image signals DS1, DS3, and DS4. Specifically, as illustrated in (b) in FIG. 24, the second auxiliary data AD2C includes data of the MSB of pixel data generated at pixels of address numbers “0” to “2” included in the word WD1 (first distributed image signal DS1), data of the MSB of pixel data generated at pixels of address numbers “5” to “7” included in the word WD3 (third distributed image signal DS3), and data of the MSB of each of pieces of pixel data generated at pixels of address numbers “8” and “9” included in the word WD4 (fourth distributed image signal DS4). Then, the data addition unit 2272C generates a second transmission image signal TS2C ((b) in FIG. 24) by adding the second auxiliary data AD2C to the second distributed image signal DS2 part of data of which is deleted at the data deletion unit 2273C.

As illustrated in (b) in FIG. 24, the data deletion unit 2273C deletes data of the LSB of one piece of pixel data (pixel data generated at the pixel of address number "4") included in the word WD2 (second distributed image signal DS2). Specifically, through addition of the second auxiliary data AD2C (8 bits) to the second distributed image signal DS2 (24 bits) of part of data of which is deleted at the data deletion unit 2273A, the second transmission image signal TS2C has a number of bits enough to allow execution of the 8 bits/10 bits conversion processing at a later stage.

Then, the received signal processing unit 62C executes the mapping decoding processing described below.

Specifically, the received signal processing unit 62C restores a distributed image signal corresponding to an optical fiber in which a transmission failure has occurred by using the second auxiliary data AD2C included in the second transmission image signal TS2C transmitted through the second optical fiber 2322. For example, when a transmission failure occurs in the first optical fiber 2321, the received signal processing unit 62C restores the first distributed image signal DS1 by using data of the MSB of pixel data generated at pixels of address numbers "0" to "2" included in the second auxiliary data AD2C. When a transmission failure occurs in the third optical fiber 2323, the received signal processing unit 62C restores the third distributed image signal DS3 by using data of the MSB of pixel data generated at pixels of address numbers "5" to "7" included in the second auxiliary data AD2C. When a transmission failure occurs in the fourth optical fiber 2324, the received signal processing unit 62C restores the fourth distributed image signal DS4 by using data of the MSB of each of pieces of pixel data generated at pixels of address numbers "8" and "9" included in the second auxiliary data AD2C. Then, the received signal processing unit 62C restores the image signals before the mapping processing at the camera head 22C by combining this restored distributed image signal and a distributed image signal extracted from a transmission image signal transmitted through an optical fiber in which no transmission failure has occurred.

When no transmission failure occurs in any of the first, third, and fourth optical fibers 2321, 2323, and 2324 other than the second optical fiber 2322, the received signal processing unit 62C does not use auxiliary data included in a transmission image signal transmitted through this optical fiber in the mapping decoding processing. Thus, auxiliary data added to a distributed image signal corresponding to this optical fiber in the auxiliary data addition processing may be any data that allows execution of the 8 bits/10 bits conversion processing at a later stage.

Figure 25:
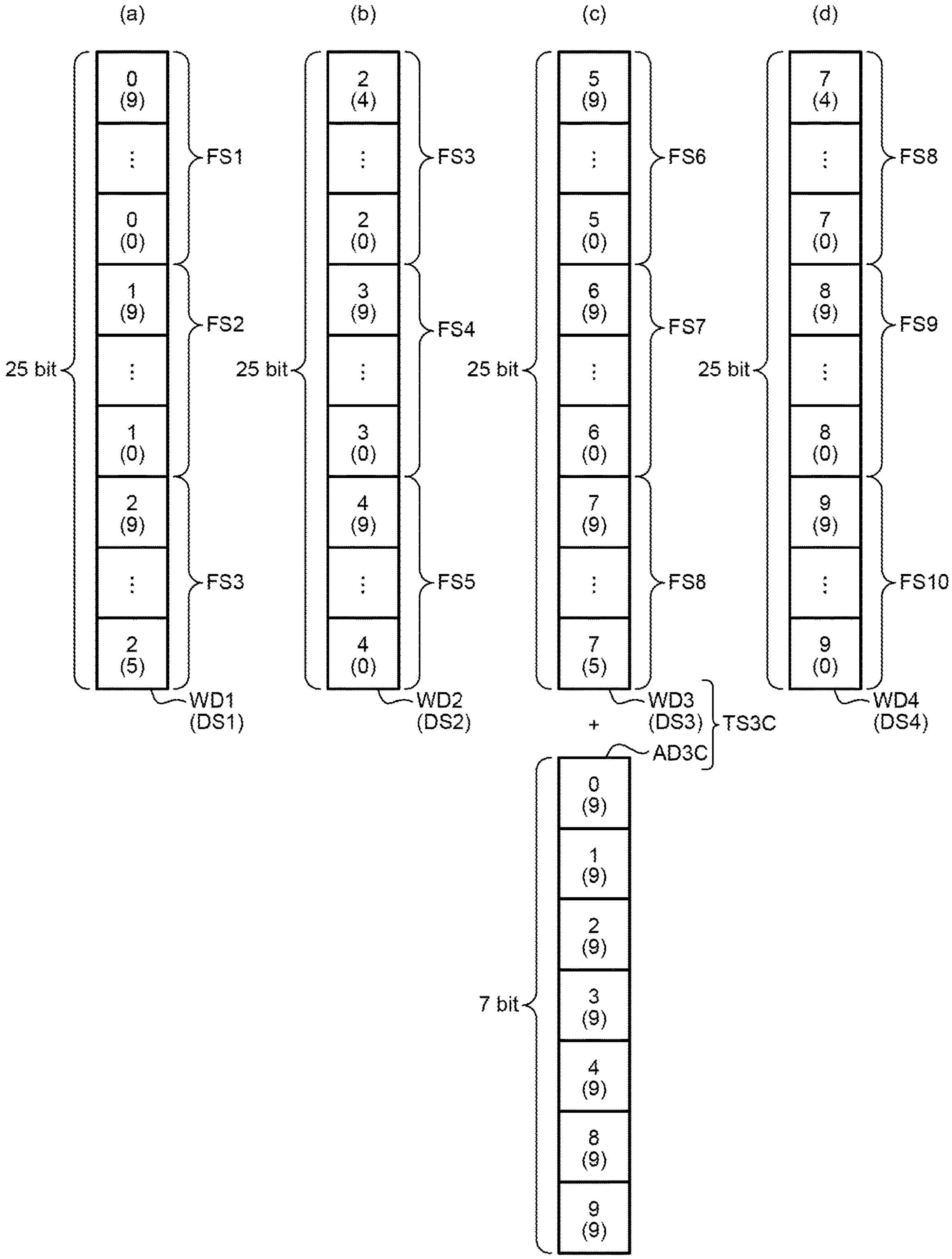
FIG. 25 is a diagram illustrating third auxiliary data added at the data addition unit when no transmission failure occurs in a third optical fiber illustrated in FIG. 21.

FIG. 25 is a diagram illustrating third auxiliary data AD3C added at the data addition unit 2272C when no transmission failure occurs in the third optical fiber 2323. Specifically, FIG. 25 corresponds to FIG. 8 (focusing on the words WD1 to WD4 illustrated in FIG. 6). For the purpose of description, FIG. 25 illustrates an example in which transmission failures have occurred in the three optical fibers of the first, second, and fourth optical fibers 2321, 2322, and 2324.

When no transmission failure occurs in the third optical fiber 2323 (when a transmission failure occurs in at least any of the first, second, and fourth optical fibers 2321, 2322, and 2324), the data addition unit 2272C uses, as the third auxiliary data AD3C of the third distributed image signal DS3, data (7 bits) of the MSB of each pixel data included in the first, second, and fourth distributed image signals DS1, DS2, and DS4. Specifically, as illustrated in (c) in FIG. 25, the third auxiliary data AD3C includes data of the MSB of pixel data generated at pixels of address numbers "0" to "2" included in the word WD1 (first distributed image signal DS1), data of the MSB of each of pieces of pixel data generated at pixels of address numbers "3" and "4" included in the word WD2 (second distributed image signal DS2), and data of the MSB of each of pieces of pixel data generated at pixels of address numbers "8" and "9" included in the word WD4 (fourth distributed image signal DS4). Then, the data addition unit 2272C generates a third transmission image signal TS3C ((c) in FIG. 25) by adding the third auxiliary data AD3C to the third distributed image signal DS3.

Then, the received signal processing unit 62C executes the mapping decoding processing described below.

Specifically, the received signal processing unit 62C restores a distributed image signal corresponding to an optical fiber in which a transmission failure has occurred by using the third auxiliary data AD3C included in the third transmission image signal TS3C transmitted through the third optical fiber 2323. For example, when a transmission failure occurs in the first optical fiber 2321, the received signal processing unit 62C restores the first distributed image signal DS1 by using data of the MSB of pixel data generated at pixels of address numbers "0" to "2" included in the third auxiliary data AD3C. When a transmission failure occurs in the second optical fiber 2322, the received signal processing unit 62C restores the second distributed image signal DS2 by using data of the MSB of each of pieces of pixel data generated at pixels of address numbers "3" and "4" included in the third auxiliary data AD3C. When a transmission failure occurs in the fourth optical fiber 2324, the received signal processing unit 62C restores the fourth distributed image signal DS4 by using data of the MSB of each of pieces of pixel data generated at pixels of address numbers "8" and "9" included in the third auxiliary data AD3C. Then, the received signal processing unit 62C restores the image signals before the mapping processing at the camera head 22C by combining this restored distributed image signal and a distributed image signal extracted from a transmission image signal transmitted through an optical fiber in which no transmission failure has occurred.

When no transmission failure occurs in any of the first, second, and fourth optical fibers 2321, 2322, and 2324 other than the third optical fiber 2323, the received signal processing unit 62C does not use auxiliary data included in a transmission image signal transmitted through this optical fiber in the mapping decoding processing. Thus, auxiliary data added to a distributed image signal corresponding to this optical fiber in the auxiliary data addition processing may be any data that allows execution of the 8 bits/10 bits conversion processing at a later stage.

Figure 26:
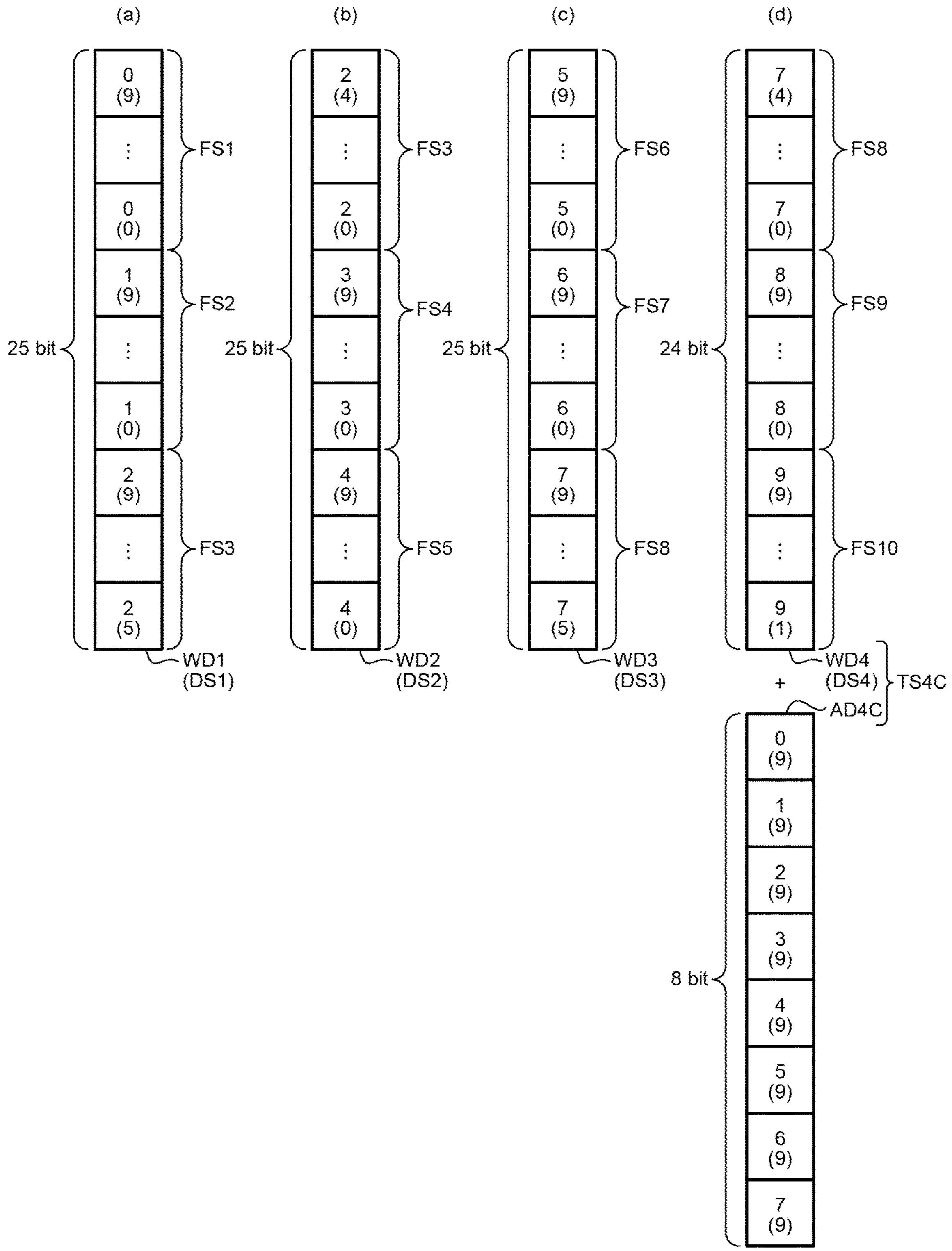
FIG. 26 is a diagram illustrating fourth auxiliary data added at the data addition unit when no transmission failure occurs in a fourth optical fiber illustrated in FIG. 21.

FIG. 26 is a diagram illustrating fourth auxiliary data AD4C added at the data addition unit 2272C when no transmission failure occurs in the fourth optical fiber 2324. Specifically, FIG. 26 corresponds to FIG. 8 (focusing on the words WD1 to WD4 illustrated in FIG. 6). For the purpose of description, FIG. 26 illustrates an example in which transmission failures have occurred in the three optical fibers of the first to third optical fibers 2321 to 2323.

When no transmission failure occurs in the fourth optical fiber 2324 (when a transmission failure occurs in at least any of the first to third optical fibers 2321 to 2323), the data addition unit 2272C uses, as the fourth auxiliary data AD4C of the fourth distributed image signal DS4, data (8 bits) of the MSB of each pixel data included in the first to third distributed image signals DS1 to DS3. Specifically, as illustrated in (d) in FIG. 26, the fourth auxiliary data AD4C includes data of the MSB of pixel data generated at pixels of address numbers “0” to “2” included in the word WD1 (first distributed image signal DS1), data of the MSB of each of pieces of pixel data generated at pixels of address numbers “3” and “4” included in the word WD2 (second distributed image signal DS2), and data of the MSB of pixel data generated at pixels of address numbers “5” to “7” included in the word WD3 (third distributed image signal DS3). Then, the data addition unit 2272C generates a fourth transmission image signal TS4C ((d) in FIG. 26) by adding the fourth auxiliary data AD4C to the fourth distributed image signal DS4 part of data of which is deleted at the data deletion unit 2273C.

As illustrated in (d) in FIG. 26, the data deletion unit 2273C deletes data of the LSB of one piece of pixel data (pixel data generated at the pixel of address number “9”) included in the word WD4 (fourth distributed image signal DS4). Specifically, through addition of the fourth auxiliary data AD4C (8 bits) to the fourth distributed image signal DS4 (24 bits) part of data of which is deleted at the data deletion unit 2273C, the fourth transmission image signal TS4C has a number of bits enough to allow execution of the 8 bits/10 bits conversion processing at a later stage.

Then, the received signal processing unit 62C executes the mapping decoding processing described below.

Specifically, the received signal processing unit 62C restores a distributed image signal corresponding to an optical fiber in which a transmission failure has occurred by using the fourth auxiliary data AD4C included in the fourth transmission image signal TS4C transmitted through the fourth optical fiber 2324. For example, when a transmission failure occurs in the first optical fiber 2321, the received signal processing unit 62C restores the first distributed image signal DS1 by using data of the MSB of pixel data generated at pixels of address numbers “0” to “2” included in the fourth auxiliary data AD4C. When a transmission failure occurs in the second optical fiber 2322, the received signal processing unit 62C restores the second distributed image signal DS2 by using data of the MSB of each of pieces of pixel data generated at pixels of address numbers “3” and “4” included in the fourth auxiliary data AD4C. When a transmission failure occurs in the third optical fiber 2323, the received signal processing unit 62C restores the third distributed image signal DS3 by using data of the MSB of pixel data generated at pixels of address numbers “5” to “7” included in the fourth auxiliary data AD4C. Then, the received signal processing unit 62C restores the image signals before the mapping processing at the camera head 22C by combining this restored distributed image signal and a distributed image signal extracted from a transmission image signal transmitted through an optical fiber in which no transmission failure has occurred.

When no transmission failure occurs in the first to third optical fibers 2321 to 2323 other than the fourth optical fiber 2324, the received signal processing unit 62C does not use auxiliary data included in a transmission image signal transmitted through this optical fiber in the mapping decoding processing. Thus, auxiliary data added to a distributed image signal corresponding to this optical fiber in the auxiliary data addition processing may be any data that allows execution of the 8 bits/10 bits conversion processing at a later stage.

When no transmission failure occurs in at least two (three at maximum) of optical fibers among the first to the fourth optical fibers 2321 to 2324, the transmission signal processing unit 224C executes any one of the auxiliary data addition processing (FIG. 23) that adds the first auxiliary data AD1C to the first distributed image signal DS1, the auxiliary data addition processing (FIG. 24) that adds the second auxiliary data AD2C to the second distributed image signal DS2 data of part of which is deleted at the data deletion processing, the auxiliary data addition processing (FIG. 25) that adds the third auxiliary data AD3C to the third distributed image signal DS3, and the auxiliary data addition processing (FIG. 26) that adds the fourth auxiliary data AD4C to the fourth distributed image signal DS4 data of part of which is deleted at the data deletion processing.

The medical observation system 1C according to the fourth embodiment described above achieves the same effect as those of the first to the third embodiments described above.

In the first to the fourth embodiments described above, the electrical-optical conversion unit 225 is provided to the camera head 22 (22A to 22C), but the present disclosure is not limited thereto. For example, the electrical-optical conversion unit 225 may be provided to the first transmission cable 23 including the connector CN2. Moreover, at least part or all of the internal configuration (function) of the transmission signal processing unit 224 (224A to 224C) as the medical signal processing device according to the present disclosure may be provided to the first transmission cable 23 including the connector CN2. In this case, an electric signal is output from the camera head 22 (22A to 22C), converted into an optical signal at the electrical-optical conversion unit 225 provided to the first transmission cable 23, and transmitted as a transmission image signal through the optical fibers 232 (signal transmission paths).

Fifth Embodiment

The following describes a fifth embodiment of the present disclosure.

In the following description, any component identical to that in the first embodiment described above is denoted by an identical reference sign, and detailed description thereof will be omitted or simplified.

In the medical observation system 1 according to the first embodiment described above, the present disclosure is applied to the endoscope 2 including the camera head 22.

In a medical observation system according to the fifth embodiment, however, the present disclosure is applied to what is called a video scope including an imaging unit at a leading end of an insertion unit of an endoscope.

Figure 27:
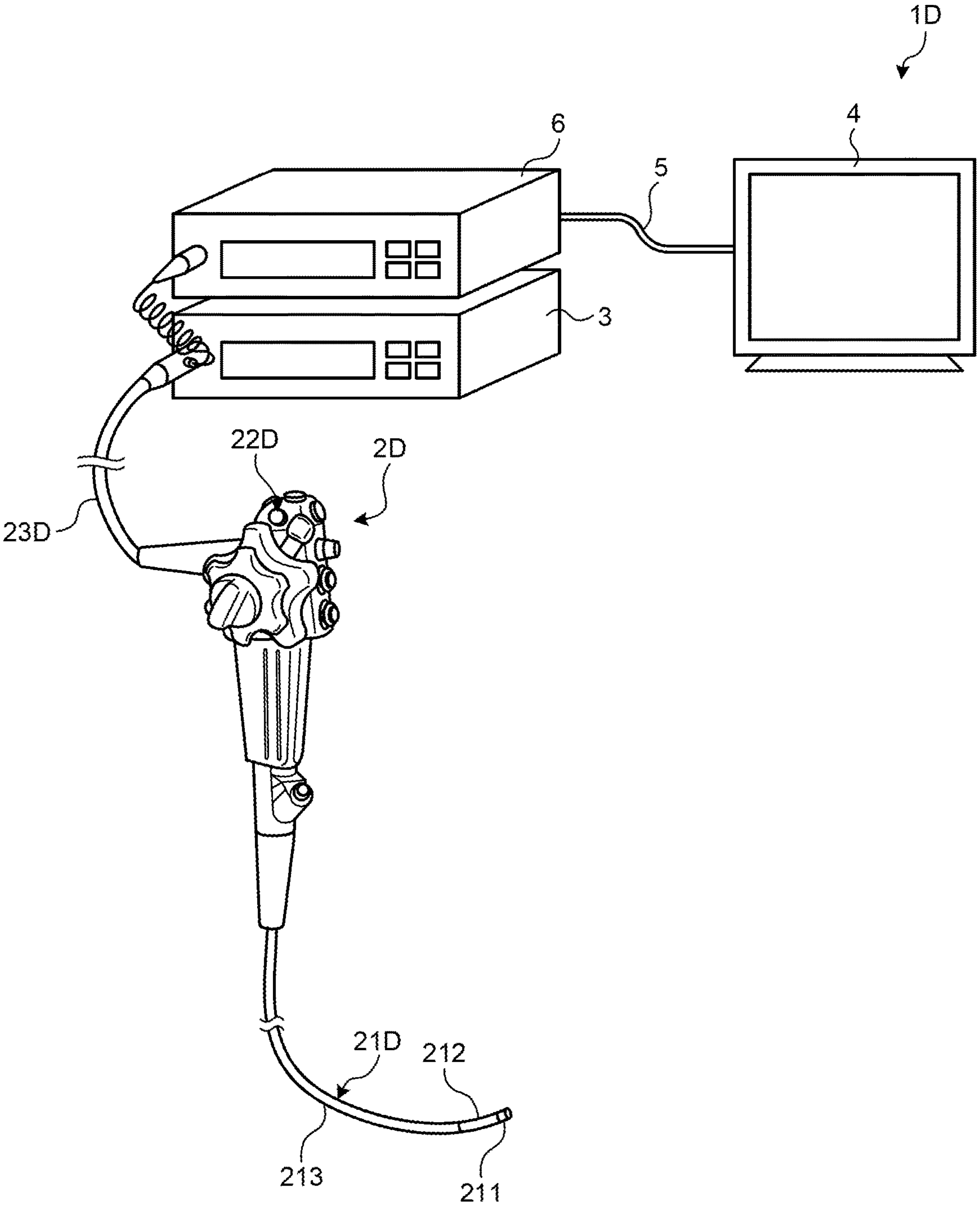
FIG. 27 is a diagram illustrating a schematic configuration of a medical observation system according to a fifth embodiment of the present disclosure.

FIG. 27 is a diagram illustrating a schematic configuration of a medical observation system 1D according to the fifth embodiment of the present disclosure.

As illustrated in FIG. 27, the medical observation system 1D according to the fifth embodiment includes an endoscope 2D configured to generate an image signal by capturing an image of the inside of the body at an observation site through an insertion unit 21D inserted into the inside of the living body and generate a plurality of transmission image signals from this image signal, the light source device 3 configured to generate illumination light to be emitted from a leading end of the endoscope 2D, the control device 6 configured to receive the transmission image signals generated at the endoscope 2D and process these transmission image signals, and the display device 4 connected with the control device 6 through the second transmission cable 5 and configured to display an image based on the image signals processed at the control device 6.

As illustrated in FIG. 27, the endoscope 2D includes the flexible elongated insertion unit 21D, an operation unit 22D connected with a base end side of the insertion unit 21D and configured to receive inputting of various operation signals, and a universal code 23D extending from the operation unit 22D in a direction different from a direction in which the insertion unit 21D extends and including various built-in cables connected to the light source device 3 and the control device 6.

As illustrated in FIG. 27, the insertion unit 21D includes a leading end part 211 including a built-in imaging unit (not illustrated) configured to generate an image signal by capturing an image of the inside of the living body, a bent part 212 that includes a plurality of bent pieces and may be freely bent, and an elongated flexible tube 213 connected with a base end side of the bent part 212.

Then, although not illustrated in detail, built-in components similar to the transmission signal processing unit 224 and the electrical-optical conversion unit 225 described in the first embodiment above are included inside the operation unit 22D. The image signal generated at the imaging unit described above is processed at this transmission signal processing unit. The universal code 23D has a configuration substantially same as the first transmission cable 23 described in the first embodiment above. Then, a plurality of transmission image signals (optical signals) processed (generated) inside of the operation unit 22D (the transmission signal processing unit and the electrical-optical conversion unit) are output to the control device 6 through the universal code 23D.

When a soft endoscope (the endoscope 2D) is used as in the fifth embodiment described above, the same effect as that of the first embodiment described above is achieved.

A built-in component identical to the transmission signal processing units 224A to 224C in the second to the fourth embodiments described above may be included inside the operation unit 22D in place of the transmission signal processing unit 224, and the control devices 6A to 6C in the second to the fourth embodiments described above may be employed in place of the control device 6.

Sixth Embodiment

The following describes a sixth embodiment of the present disclosure.

In the following description, any component identical to that in the first embodiment described above is denoted by an identical reference sign, and detailed description thereof will be omitted or simplified.

In the medical observation system 1 according to the first embodiment described above, the present disclosure is applied to the endoscope 2 including the camera head 22.

In a medical observation system according to the sixth embodiment, however, the present disclosure is applied to a surgical microscope configured to capture an enlarged image of a predetermined viewing region in the inside of a subject (the inside of a living body) or on the surface of the subject (the surface of the living body).

Figure 28:
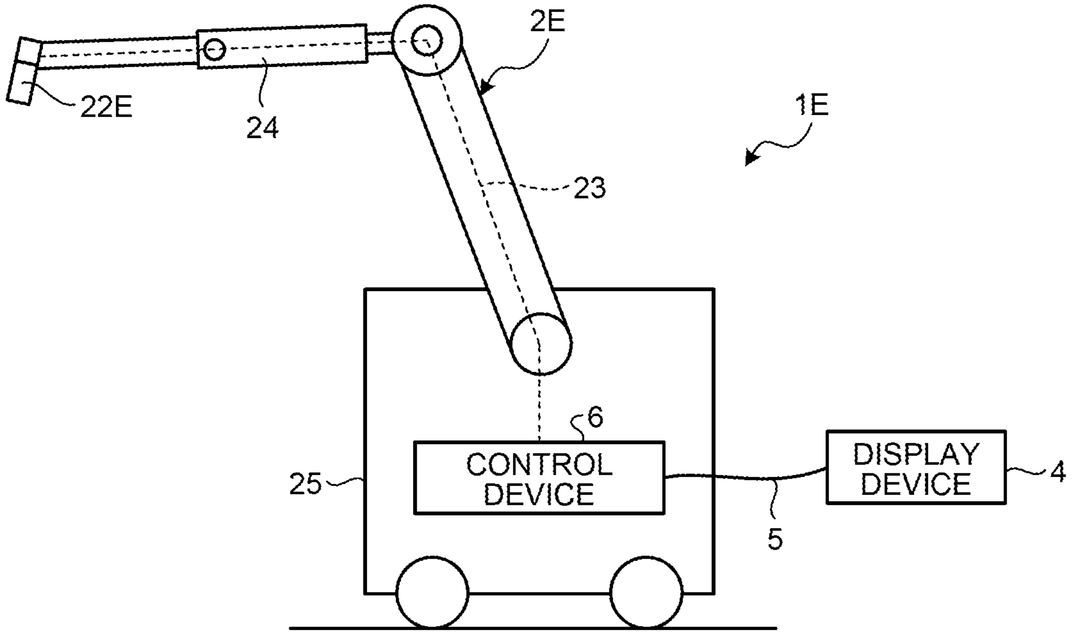
FIG. 28 is a diagram illustrating a schematic configuration of a medical observation system according to a sixth embodiment of the present disclosure.

FIG. 28 is a diagram illustrating a schematic configuration of a medical observation system 1E according to the sixth embodiment of the present disclosure.

As illustrated in FIG. 28, the medical observation system 1E according to the sixth embodiment includes a surgical microscope 2E configured to generate an image signal by capturing an image for observing an object and generate a plurality of transmission image signals from this image signal, the control device 6 configured to receive the transmission image signals generated at the surgical microscope 2E and process these transmission image signals, and the display device 4 connected with the control device 6 through the second transmission cable 5 and configured to display an image based on the image signals processed at the control device 6.

As illustrated in FIG. 28, the surgical microscope 2E includes a microscope unit 22E configured to generate an image signal by capturing an enlarged image of a small site of the object and generate a plurality of transmission image signals from this image signal, a support unit 24 connected with a base end part of the microscope unit 22E and including an arm rotatably supporting the microscope unit 22E, and a base unit 25 rotatably holding a base end part of the support unit 24 and movable on a floor surface.

As illustrated in FIG. 28, the control device 6 is installed in the base unit 25.

Instead of being provided movably on the floor surface, the base unit 25 may be fixed on, for example, a ceiling or a wall surface to support the support unit 24. The base unit 25 may include a light source unit configured to generate illumination light to be emitted to the object from the surgical microscope 2E.

Although not illustrated in detail specifically, the microscope unit 22E includes an imaging unit configured to generate an image signal by capturing an image of the inside of the living body, and built-in components similar to the transmission signal processing unit 224 and the electrical-optical conversion unit 225 described in the first embodiment above. The image signal generated at the imaging unit is processed at the transmission signal processing unit. Then, a plurality of transmission image signals (optical signals) processed (generated) at the microscope unit 22E (the transmission signal processing unit and the electrical-optical conversion unit) are output to the control device 6 through the first transmission cable 23 wired along the support unit 24.

When the surgical microscope 2E is used as in the sixth embodiment described above, the same effect as that of the first embodiment described above is achieved.

A built-in component similar to the transmission signal processing units 224A to 224C in the second to the fourth embodiments described above may be included inside the microscope unit 22E in place of the transmission signal processing unit 224, and the control devices 6A to 6C in the second to the fourth embodiments described above may be employed in place of the control device 6.

Other Embodiments

The configurations to achieve the present disclosure are described above, but the present disclosure is not limited to the first to the sixth embodiments described above.

In the first to the sixth embodiments described above, a plurality of transmission image signals are transmitted as optical signals from the camera heads 22 and 22A to 22C, the operation unit 22D, and the microscope unit 22E to the control devices 6 and 6A to 6C, but the present disclosure is not limited thereto. The transmission image signals may be transmitted as electric signals. In other words, the optical fibers 232 as signal transmission paths according to the present disclosure included in the first transmission cable 23 and the universal code 23D may be replaced with electric wires. In this case, the electrical-optical conversion unit 225 and the optical-electrical conversion unit 61 are omitted.

Figure 29:
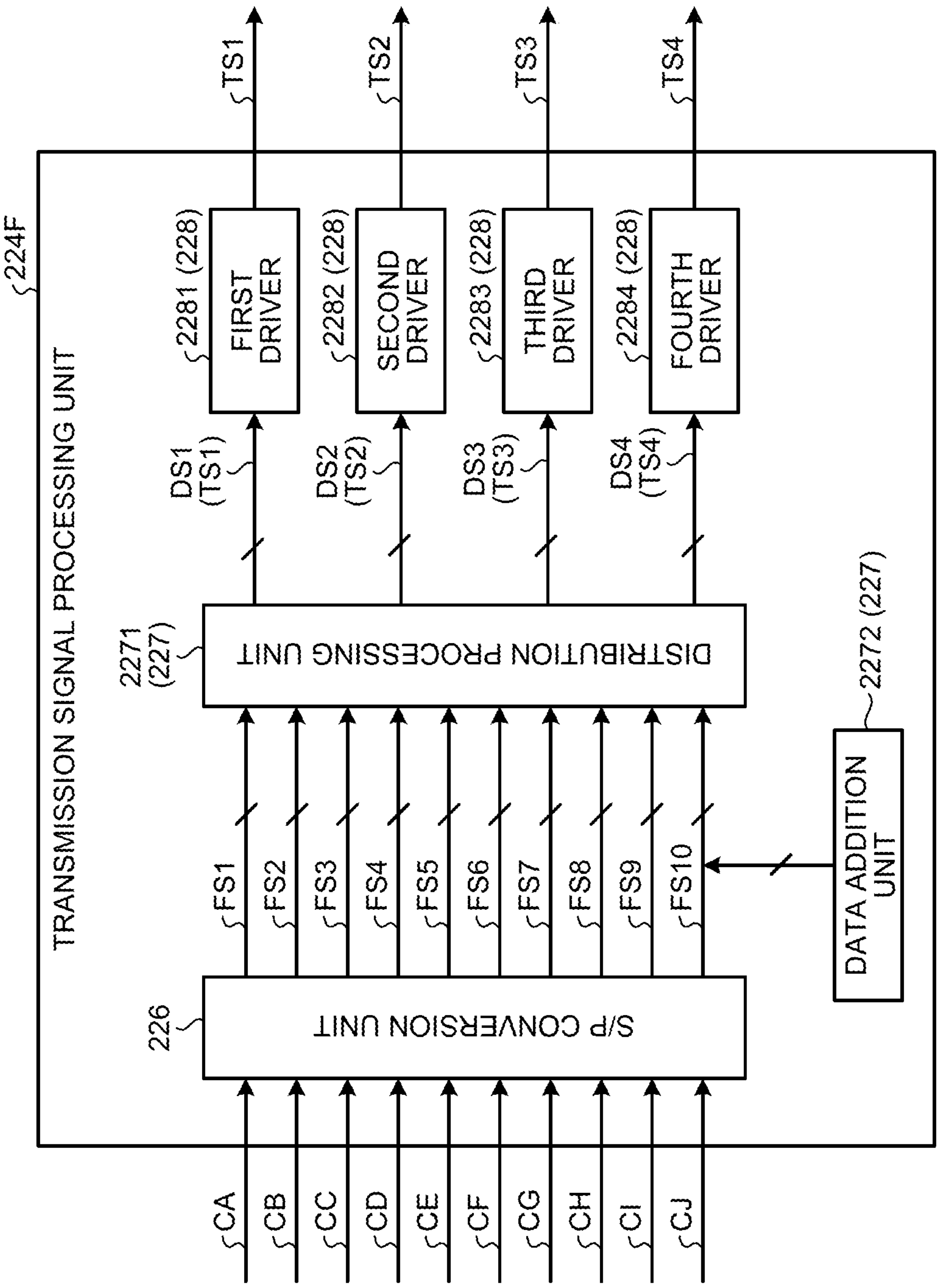
FIG. 29 is a diagram illustrating a modification of the first to the sixth embodiments of the present disclosure.

FIG. 29 is a diagram illustrating a modification of the first to the sixth embodiments of the present disclosure. Specifically, FIG. 29 is a diagram illustrating the configuration of a transmission signal processing unit 224F according to this modification.

For the purpose of description, FIG. 29 illustrates the transmission signal processing unit 224F as a modification of the transmission signal processing unit 224 described in the first embodiment above.

In the transmission signal processing units 224 and 224A to 224C according to the first to the sixth embodiments described above, the auxiliary data addition processing is executed after the mapping processing, but the present disclosure is not limited thereto. As executed by the transmission signal processing unit 224F illustrated in FIG. 29, the mapping processing may be executed after the auxiliary data addition processing (in which auxiliary data is added to the first to the tenth image signals FS1 to FS10, and the first to the fourth transmission image signals TS1 to TS4 are generated by distributing the first to the tenth image signals FS1 to FS10 to which this auxiliary data is added).

A medical signal processing device according to the present disclosure receives an image signal in accordance with a result of examining the inside of a subject and generates a plurality of transmission image signals from the image signal. The transmission image signals each include a plurality of distributed image signals obtained by distributing the image signal. At least any one of the transmission image signals includes, as auxiliary data, data of at least part of distributed image signals different from the distributed image signals included in this transmission image signal. Then, the transmission image signals are each transmitted to an external medical control device through a plurality of respective signal transmission paths.

With this configuration, when a transmission failure occurs in a signal transmission path but not in all of the signal transmission paths, the medical control device may restore, based on auxiliary data included in a transmission image signal transmitted through a signal transmission path in which no transmission failure has occurred, distributed image signals included in another transmission image signal corresponding to the signal transmission path in which a transmission failure has occurred. Accordingly, a display image signal may be appropriately generated based on distributed image signals included in a transmission image signal transmitted through a signal transmission path in which no transmission failure has occurred and a distributed image signal restored as described above.

Thus, the medical signal processing device according to the present disclosure provides an effect of achieving a simplified structure without a redundant signal transmission path that is unnecessary when no transmission failure occurs, and achieving continuous display of an image suitable for observation when a transmission failure occurs in a signal transmission path.

A medical observation system according to the present disclosure includes the medical signal processing device and the medical control device described above, and thus provides an effect similar to the above-described effect of the medical signal processing device.

It should be understood by those skilled in the art that various modifications, combinations, sub-combinations and alterations may occur depending on design requirements and other factors insofar as they are within the scope of the appended claims or the equivalents thereof.

What is claimed is:

1. A medical signal processing device for receiving an image signal in accordance with a result of imaging inside of a subject and processing the image signal, the medical signal processing device comprising:

signal processing circuitry configured to generate a first transmission image signal and a second transmission image from the image signal, wherein the first transmission image signal includes a first distributed image signal obtained by distributing the image signal, the second transmission image signal includes a second distributed image signal obtained by distributing the image signal and data of at least part of the first distributed image signal, and the first transmission image signal is transmitted to an external medical control device through a first signal transmission path and the second transmission image signal is transmitted to the external medical control device through a second signal transmission path, wherein the medical control device is configured to receive the first transmission image signal and the second transmission image signal, wherein the medical control device includes:

processing circuitry configured to:

detect a signal transmission failure in the first signal transmission path, and restore the first distributed image based on the data of at least part of the first distributed image signal included in the second transmission image signal.

2. The medical signal processing device according to claim 1, wherein the processing circuitry is further configured to restore the image signal based on the first distributed image signal included in the first distributed image signal and the second distributed image signal included in the first distributed image signal when the signal transmission failure is not detected.

3. The medical signal processing device according to claim 2, wherein the signal processing circuitry is configured to generate the first distributed image signal and the second distributed image signal by distributing the image signal, and add the data of at least part of the first distributed image signal to the second distributed image signal.

4. The medical signal processing device according to claim 2, wherein the signal processing circuitry is configured to:

add the data of at least part of the first distributed image signal to the image signal, and generate the first transmission image signal and the second transmission image signal by distributing the image signal to which the data of at least part of the first distributed image signal is added.

5. The medical signal processing device according to claim 2, wherein the first distributed image signal and the second distributed image signal include pixel data of each pixel arrayed at a constant interval among pixels sequentially arrayed in a predetermined direction in an image made of pixels arrayed in a matrix, and the second transmission image signal includes at least data at a bit position of a most significant digit of each pixel data included in the first distributed image signal.

6. The medical signal processing device according to claim 2, wherein the amount of data of the first transmission image signal and the second transmission image signal is predetermined, and the signal processing circuitry is further configured to delete, in accordance with the amount of the data of at least part of the first distributed image signal, part of the second distributed image signal included in the second transmission image signal.

7. The medical signal processing device according to claim 6, wherein the first distributed image signal and the second distributed image signal include pixel data of each pixel arrayed at a constant interval among pixels sequentially arrayed in a predetermined direction in an image made of pixels arrayed in a matrix, and data of part of the second distributed image signal deleted at the signal processing circuitry is at least data at a bit position of a least significant digit of each pixel data included in the second distributed image signal.

8. The medical signal processing device according to claim 2, wherein the signal processing circuitry is further configured delete, based on transmission failure information indicating a signal transmission failure in the first signal transmission path, data of part of the second distributed image signal.

9. The medical signal processing device according to claim 2, wherein the amount of data of the first transmission image signal and the second transmission image signal is same, and the amount of data of the first distributed image signal and the second distributed image signal is also same.

10. A medical observation system comprising:

a medical signal processing device for receiving an image signal in accordance with a result of imaging inside of a subject and processing the image signal, the medical signal processing device including:

signal processing circuitry configured to generate a first transmission image signal and a second transmission image from the image signal, wherein the first transmission image signal includes a first distributed image signal obtained by distributing the image signal, the second transmission image signal includes a second distributed image signal obtained by distributing the image signal and data of at least part of the first distributed image signal, and the first transmission image signal is transmitted to an external medical control device through a first signal transmission path and the second transmission image signal is transmitted to the external medical control device through a second signal transmission path; and a medical control device configured to receive the first transmission image signal and the second transmission image signal, wherein the medical control device includes:

processing circuitry configured to:

detect a signal transmission failure in the first signal transmission path, and restore the first distributed image based on the data of at least part of the first distributed image signal included in the second transmission image signal.

11. The medical observation system according to claim 10, further comprising:

a notification device configured to give notification of predetermined information; and a notification control circuitry configured to cause the notification device to give notification of the predetermined information when a transmission failure is detected.

12. The medical observation system according to claim 10, wherein the first signal transmission path and the second signal transmission path include a light transmission path through which an optical signal is transmitted, and the medical observation system includes:

an electrical-optical converter configured to convert a plurality of electric signals based on the first transmission image signal and the second transmission image signal into a plurality of respective optical signals, and output the optical signals to the first signal transmission path and the second signal transmission path, and an optical-electrical converter configured to convert the optical signals received through the first signal transmission path and the second signal transmission path into a plurality of respective electric signals, and output the electric signals to the medical control device.

* * * * *